(12) United States Patent
Rose et al.

(10) Patent No.: US 8,025,502 B2
(45) Date of Patent: Sep. 27, 2011

(54) LIGHT GUIDE FOR DENTISTRY APPLICATIONS

(75) Inventors: Eric P. Rose, Tarzana, CA (US); Bruce Sargeant, Orange, CA (US); Douglas H. Grambush, Corona del Mar, CA (US); Stuart Karten, Venice, CA (US); Dennis Schroeder, Hermosa Beach, CA (US)

(73) Assignee: Discus Dental, LLC, Culver City, CA (US)

( * ) Notice: Subject to any disclaimer, the term of this patent is extended or adjusted under 35 U.S.C. 154(b) by 0 days.

(21) Appl. No.: 11/173,734

(22) Filed: Jun. 30, 2005

(65) Prior Publication Data

US 2006/0029901 A1 Feb. 9, 2006

Related U.S. Application Data

(63) Continuation-in-part of application No. 29/220,680, filed on Jan. 4, 2005, now Pat. No. Des. 537,192, which is a continuation-in-part of application No. 29/220,679, filed on Jan. 4, 2005, now Pat. No. Des. 543,934, which is a continuation-in-part of application No. 29/220,712, filed on Jan. 4, 2005, now Pat. No. Des. 538,459, which is a continuation-in-part of application No. 29/232,670, filed on Jun. 22, 2005, now Pat. No. Des. 538,960, which is a continuation-in-part of application No. 29/232,671, filed on Jun. 22, 2005, now Pat. No. Des. 539,956.

(60) Provisional application No. 60/585,224, filed on Jul. 2, 2004, provisional application No. 60/641,462, filed on Jan. 4, 2005, provisional application No. 60/647,725, filed on Jan. 26, 2005, provisional application No. 60/647,723, filed on Jan. 26, 2005, provisional application No. 60/658,517, filed on Mar. 3, 2005, provisional application No. 60/647,580, filed on Jan. 26, 2005, provisional application No. 60/641,469, filed on Jan. 4, 2005, provisional application No. 60/641,461, filed on Jan. 4, 2005, provisional application No. 60/641,468, filed on Jan. 4, 2005, provisional application No. 60/647,612, filed on Jan. 26, 2005, provisional application No. 60/647,593, filed on Jan. 26, 2005, provisional application No. 60/604,577, filed on Aug. 25, 2004, provisional application No. 60/594,297, filed on Mar. 25, 2005, provisional application No. 60/631,267, filed on Nov. 26, 2004, provisional application No. 60/594,327, filed on Mar. 30, 2005, provisional application No. 60/664,696, filed on Mar. 22, 2005.

(51) Int. Cl.
*A61C 1/00* (2006.01)
*A61C 3/00* (2006.01)
*A61C 17/06* (2006.01)
*A61C 5/00* (2006.01)

(52) U.S. Cl. .............. 433/29; 433/31; 433/140

(58) Field of Classification Search .............. 433/29, 433/215, 136–140, 93, 31; 362/804, 573, 362/558, 311.08; 250/580; 600/237–245; 606/15–18, 208; 385/116, 117, 124
See application file for complete search history.

(56) References Cited

U.S. PATENT DOCUMENTS 3,916,880 A   11/1975   Schroer
(Continued)

FOREIGN PATENT DOCUMENTS

WO   WO2004108003 A1 * 12/2004

*Primary Examiner* — Todd Manahan
*Assistant Examiner* — Yogesh Patel

(57) ABSTRACT

The present invention relates to a light guide for a lamp for dentistry procedures. The light guide provides an optical channel between a light source and a dental substrate. The light guide may be a one-patient use light guide including a recording medium to record the time used. The light guide further provides protection for a patient's soft tissues during treatment.

27 Claims, 12 Drawing Sheets

U.S. PATENT DOCUMENTS

| | | | |
|---|---|---|---|
| 4,592,344 A * | 6/1986 | Scheer | 600/242 |
| 4,605,927 A * | 8/1986 | Katz et al. | 340/825.19 |
| 4,952,143 A | 8/1990 | Becker et al. | |
| 5,316,473 A | 5/1994 | Hare | |
| 5,473,524 A * | 12/1995 | Behringer | 362/294 |
| 5,523,745 A * | 6/1996 | Fortune et al. | 340/825.19 |
| 5,634,711 A * | 6/1997 | Kennedy et al. | 362/119 |
| 6,077,073 A * | 6/2000 | Jacob | 433/29 |
| 6,193,510 B1 * | 2/2001 | Tsimerman | 433/29 |
| 6,391,283 B1 | 5/2002 | Jensen et al. | |
| 6,485,301 B1 * | 11/2002 | Gemunder et al. | 433/29 |
| 6,494,827 B1 * | 12/2002 | Matsumoto et al. | 600/118 |
| 6,511,321 B1 * | 1/2003 | Trushkowsky et al. | 433/164 |
| 6,514,075 B1 | 2/2003 | Jacob | |
| 6,536,068 B1 * | 3/2003 | Yang et al. | 15/105 |
| 6,692,251 B1 | 2/2004 | Logan et al. | |
| 6,733,290 B2 | 5/2004 | West et al. | |
| 6,880,954 B2 | 4/2005 | Ollett et al. | |
| 2001/0046652 A1 * | 11/2001 | Ostler et al. | 433/29 |
| 2002/0097400 A1 * | 7/2002 | Jung et al. | 356/419 |
| 2002/0168603 A1 * | 11/2002 | Cao | 433/29 |
| 2002/0182563 A1 | 12/2002 | Boutoussov et al. | |
| 2003/0049585 A1 * | 3/2003 | Severance | 433/29 |
| 2003/0115694 A1 | 6/2003 | Pace | |
| 2003/0143512 A1 * | 7/2003 | Hirsch et al. | 433/93 |
| 2004/0015079 A1 * | 1/2004 | Berger et al. | 600/437 |
| 2004/0043351 A1 | 3/2004 | Logan et al. | |
| 2004/0053190 A1 * | 3/2004 | Lin | 433/29 |
| 2004/0076926 A1 * | 4/2004 | Baughman | 433/215 |
| 2004/0267166 A1 * | 12/2004 | Ooshima et al. | 600/590 |
| 2005/0000044 A1 * | 1/2005 | Hilscher et al. | 15/22.1 |
| 2005/0196721 A1 * | 9/2005 | Jackson et al. | 433/29 |
| 2005/0239018 A1 * | 10/2005 | Green et al. | 433/140 |

* cited by examiner

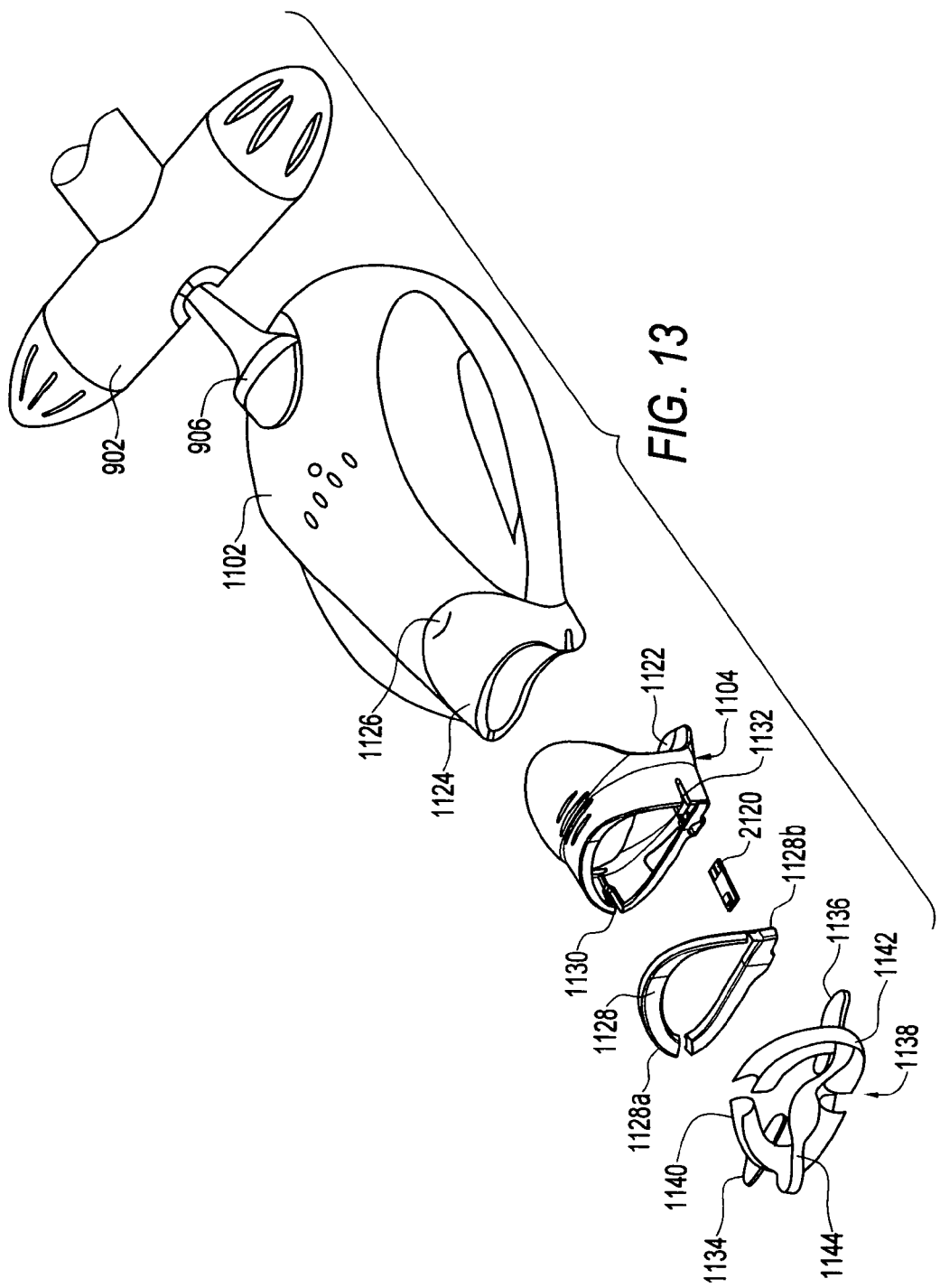

LIGHT GUIDE FOR DENTISTRY APPLICATIONS

CROSS-REFERENCE TO RELATED APPLICATIONS

This application claims the benefit of U.S. provisional patent application Ser. No. 60/585,224, filed Jul. 2, 2004, entitled "Dental Light Devices With Phase Change Heat Sink"; 60/641,462, filed Jan. 4, 2005, entitled "Boom Hinge For A Dental Lamp"; 60/647,725, filed Jan. 26, 2005, entitled "Automatic Control for a Dental Whitening Lamp"; 60/647,723, filed Jan. 26, 2005, entitled "Boom Hinge For A Dental Lamp"; 60/658,517, filed Mar. 3, 2005, entitled "Apparatus and Method For Radiation Spectrum Shifting in Dentistry Applications"; 60/641,469, filed Jan. 4, 2005, entitled "Lamp For Dentistry Applications"; 60/647,580, filed Jan. 26, 2005, entitled "Light Guide For Dental Whitening Lamp"; 60/641,461, filed Jan. 4, 2005, entitled "Support Structure For A Dental Lamp"; 60/641,468, filed Jan. 4, 2005, entitled "Light Guide For A Dental Whitening Lamp"; 60/647,612, filed Jan. 26, 2005, entitled "Light Path Apparatus For A Dental Lamp"; 60/647,593, filed Jan. 26, 2005, entitled "Support Structure For A Dental Lamp"; 60/604,577, filed Aug. 25, 2004, entitled "Lip Retractors"; 60/594,297, filed Mar. 25, 2005, entitled "Curing Light Having A Detachable Tip"; 60/631,267, filed Nov. 26, 2004, entitled "Curing Light Having A Reflector"; 60/594,327, filed on Mar. 30, 2005, entitled, "Curing Light"; and 60/664,696, filed Mar. 22, 2005, entitled "Curing Light Having A Detachable Tip"; the contents of all of which are hereby incorporated by reference.

The current application is a continuation-in-part of the following U.S. design patent application Ser. Nos. Dentistry Applications"; 29/220,680, filed Jan. 4, 2005, now U.S. Pat. No. Des. 537,192 entitled "Light Guide For Dentistry Applications"; 29/220,679, filed Jan. 4; 2005, now U.S. Pat. No. Des. 543,943 entitled "Power Pack For Dentistry Applications"; 29/220,712, filed Jan. 4, 2005, now U.S. Pat. No. Des. 538,459 entitled "Support Structure For A Lamp For Dentistry"; 29/232,670 filed Jun. 22, 2005, now U.S. Pat. No. Des. 538,960 entitled "Support Structure For Dental Applications"; and 29/232,671, filed Jun. 22, 2005, now U.S. Pat. No. Des. 539,956 entitled "Support Structure for Dental Applications"; the contents of all of which are hereby incorporated by reference.

The present application includes claims that may be related to the claims of co-pending U.S. patent application Ser. No. 11/173,731, to be concurrently filed, entitled "Support System for Dentistry"; co-pending U.S. patent application Ser. No. 11/174,363, to be concurrently filed, entitled "Automatic Control for Dental Applications"; and co-pending U.S. patent application Ser. No. 11/173,709, to be concurrently filed, entitled "Voice Alert for Dentistry Applications"; the contents of all of which are hereby incorporated by reference.

FIELD OF THE INVENTION

This invention relates to lamp systems used in dentistry. Specifically, this invention relates to lamp systems used in dental curing or dental whitening.

BACKGROUND OF THE INVENTION

A tooth is comprised of an inner dentin layer and an outer hard enamel that is coated with a protective layer called the acquired pellicle. The enamel layer is composed of hydroxyapatite crystals that create a somewhat porous surface. The pellicle or the enamel can become stained or discolored. It is believed that the porous nature of the enamel layer is what allows staining agents and discoloring substances to permeate the enamel and discolor the tooth.

Tooth discoloration has a number of causes. For example, the teeth may become stained by coffee or tea drinking, or by the use of tobacco products, or by drinking water with a high mineral content.

One solution to the staining problem is through tooth bleaching. Some dentifrices, like toothpastes, gels, and powders, contain active oxygen or hydrogen peroxide liberating bleaching agents including peroxides, percarbonates and perborates of the alkali and alkaline earth metals or complex compounds containing hydrogen peroxide.

Dental bleaching can be done either in a dental office or at home. Bleaching in a dental office generally employs compositions activatable with the aid of light sources having the appropriate wavelength outputs in order to speed up the process. Additionally, the bleaching compositions used in a dental office typically contain a higher percentage concentration of bleaching agents than the bleaching compositions found in home applications.

In addition to staining, tooth decay, resulting in cavities or other damages can also result. In the field of tooth restoration and repair, dental cavities are often filled and/or sealed with compounds that are photosensitive, either to visible and/or ultraviolet light. These compounds, commonly known as light-curable compounds, are placed within dental cavity preparations or onto dental surfaces and are cured when exposed to light from a dental curing light device.

Unlike dental curing and imaging processes, which are generally relatively fast processes, dental bleaching takes a much longer time, sometimes amounting to more than an hour per office visit. On the other hand, dental restoration is often an unwelcome experience. Therefore, it is advantageous that a person undergoing the processes, either dental restoration or bleaching, be as comfortable as possible.

The process is generally performed in a dentist's chair. Typically a dentist's chair has a wide range of adjustability such that a patient may be placed in a wide range of positions from a nearly full reclining position to a nearly upright position. In order to effectively accomplish the whitening or restoration process, a light source needs to be aligned with the mouth. The wide range of dentist's chair positions can make this alignment difficult.

Further considerations in the process of dental procedures include the ability to maintain cleanliness of the light source, and particularly of any part that comes into contact with the patient. Further, the process of whitening is, for example, optimized, that is, the light source is on as long as necessary to whiten the teeth to the desired degree. Still further, it is desirable that the light source be as efficient as possible. An efficient lamp tends to be cooler and therefore safer than an inefficient lamp. Also, an efficient lamp requires less energy to run than an inefficient lamp.

It remains desirable to have an efficient and comfortable apparatus and method for dental whitening, curing and imaging.

SUMMARY OF THE INVENTION

The present invention relates to a light guide for a light system for dentistry procedures. The light guide includes at least one formation for positioning it with respect to a light system, and also provides an optical channel between a light source and a dental substrate.

The present invention also relates to an alignment system to facilitate faster patient set up and optimal results in a dental process.

According to one embodiment of the invention, the light guide includes a first end adapted to be coupled to a light source and a second end adapted to be coupled to a reference device.

According to one aspect of the invention, the light system includes at least one formation adapted to inter-engage with at least one formation of the light guide when the light system and the light guide are apposed. The formations provide, according to one embodiment of the invention, a secure, removable connection between the housing and the light guide.

In another aspect, the reference device includes at least one formation adapted to inter-engage with at least one formation of the light guide when the light guide and the reference device are apposed. The reference device may be a lip retracting device adapted to retract the lips of a subject patient so as to provide an un-obstructed optical path between the second end of the light guide and a tooth surface of the subject patient.

In one embodiment, the light guide includes a formation adapted to removably couple the light guide to a reference device for positioning the light guide, and consequently the lamp head and the light source, in a substantially constant position and orientation with respect to a target.

The present invention also includes methods and apparatus for directing coupling light from a light source to a dental target having various desirable features and improvements.

According to a first embodiment of the invention, a tubular light guide is coupled to a dental whitening, curing light or imaging source that includes at least one source of light such as, for example, an ultraviolet light source for activating a dental compound whitening agent, cleaning and/or bleaching agent, or a composite filling materials, or a light source for producing an image of the tooth or teeth of a patient, either by direct imaging, for example, using x-rays, or by indirect imaging or trans-illumination.

In one aspect of the invention, according to various embodiments discussed below, a path is provided within the tubular light guide from the light source to a target such as a whitening compound disposed on a tooth surface or a filling compound residing either on the surface or in the cavity of a tooth. According to one embodiment, the light path includes a light source and a coupling medium such as a light guide, between the light source and a target.

In one embodiment, the light guide includes a hollow interior. The hollow interior may be filled with ambient air. Accordingly light applied to the light guide at the first end by the light source is transmitted through the air within the hollow interior. In various other embodiments of the invention, the light guide may include a wide variety of dielectric media including, but not limited to, silicon glass dielectric media, quartz glass dielectric media, polymer dielectric media, oil dielectric media, water dielectric media, and other dielectric media, and including combinations thereof. In addition, the light guide may include a region of vacuum dielectric. Depending on the requirement of a particular dental process and patient for light coupling, any appropriate light conducting medium is considered to be contemplated within the scope of the invention.

In one embodiment, the light guide minimizes the evaporation of any treatment composition applied to the teeth and may reduce sensitivity.

In another embodiment of the light guide, the light guide may be formed of a polymer material having a spectral absorption characteristic such that visible light readily passes through walls of the light guide, while ultraviolet light is either absorbed by the walls or, for example, is reflected from the internal surfaces of the light guide. By allowing the transmission of visible light the light guide facilitates the installation of the light guide since the teeth of the patient may be quite visible through the walls of the light guide. By absorbing or reflecting light of ultraviolet wavelengths, the light guide serves to contain the ultraviolet radiation directed therethrough and to shield local soft tissues from the effects of such ultraviolet radiation.

In another embodiment of the invention, the light guide is adapted to be limited to use in the treatment of a single dental patient. According to one embodiment, a single-use light guide includes a write once read many times (WORM) memory device. In a particular aspect of the invention, the WORM memory device is adapted to receive a signal related to a duration of use of a related instance of a light guide, and to substantially indelibly record such the information content of the signal for later use by a control subsystem of a light source.

In a further embodiment of the invention, a plurality of light guides each having an output end of a respective size, wherein the size of a particular output end corresponds to a mouth size of a particular patient or class of patients. For example, light guides in various embodiments may be provided that are most appropriate to be used by a large adult, a small adult, or a child.

According to various embodiments of the invention, the light guide includes air vents for patient breathing comfort during the bleaching or curing treatment.

The material of the light guide may be chosen to absorb and/or reflect light of one or more ranges of wavelength that impinges on the tubular inner surface. Consequently, according to one aspect of the invention, the light guide reduces the degree to which light of the subject of wavelengths escapes from the system except through the distal aperture of the light guide.

According to one embodiment of the invention, a light guide is adapted for use by a single patient and is thereafter disposable. In one exemplary embodiment, a control mechanism may be provided to inhibit the use of a light guide on additional patients after it has been once used. Another aspect of the control mechanism is that the inhibition occurs during the attachment process of the light guide to the lamp system.

One embodiment of the invention effects control of light guide usage by including a recording medium in the light guide, and a signal generating device elsewhere in the lamp system. In one aspect, the invention includes receipt by the recording medium of a signal from the signal generating device, and recording of a record of the recording medium corresponding to the received signal to produce a substantially permanent signal record. In another aspect of the invention, the substantially permanent signal record is read by a medium reading device and a condition of use of the particular light guide containing the recording medium is ascertained. Based on the condition of use indicated by the record, as read, a control device external to the light guide serves to allow or inhibit activation of the light source.

In one embodiment of the invention, the signal generating and record reading devices may be located within the lamp housing. In another embodiment of the invention, one or more of the signal generating and record reading devices are located external to the lamp head housing.

In one embodiment of the invention, the signal from the signal generating source may be received at the recording medium by way of an electromechanical coupling. In another embodiment of the invention, the signal from the signal generating source may be received at the recording medium by way of an optical communication channel. In a still further embodiment of the invention, the signal from the signal generating source is received at the recording medium by way of a mechanical communication channel, an acoustic communication channel, a radiofrequency communication channel, or any other communication medium appropriate the particular invention embodiment.

The present invention together with the above and other advantages may best be understood from the following detailed description of the embodiments of the invention illustrated in the drawings.

BRIEF DESCRIPTION OF THE DRAWINGS

FIG. 13 shows an exploded view of one embodiment of the present invention, including a light guide, a lamp system and a lip retracting device;

DETAILED DESCRIPTION OF INVENTION

Figure 1:
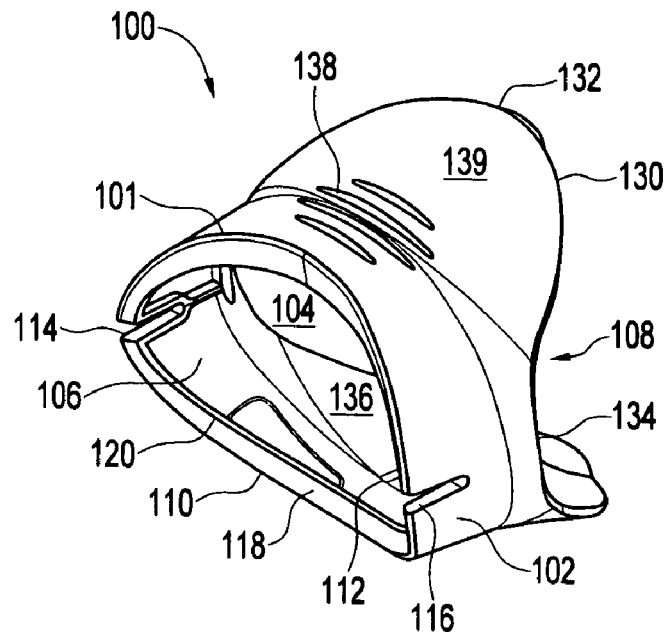
FIG. 1 shows, in perspective view, a light guide according to one embodiment of the invention.

The detailed description set forth below is intended as a description of the presently exemplified light guide for dentistry and related systems provided in accordance with aspects of the present invention and is not intended to represent the only forms in which the present invention may be prepared or utilized. The description sets forth the features and the steps for preparing and using the light guide for dentistry and related systems of the present invention. It is to be understood, however, that the same or equivalent functions and components included in the light guide and related systems may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the exemplified methods, devices and materials are now described.

All publications mentioned herein are incorporated herein by reference for the purposes of describing and disclosing, for example, the compositions and methodologies that are described in the publications which might be used in connection with the presently described invention. The publications listed or discussed above, below and throughout the text are provided solely for their disclosure prior to the filing date of the present application. Nothing herein is to be construed as an admission that the inventors are not entitled to antedate such disclosures by virtue of prior invention.

The present invention is directed to dentistry apparatus, including an apparatus and method for dental whitening, curing, imaging and/or examination that is efficient, comfortable for the patient and further includes improved safety, maintenance and operating features. One way of enabling, for example, an effective activation of a dental whitening or filling compound is to position a light source to fully illuminate a tooth surface being treated.

Moreover, since light intensity varies as the inverse cube of distance from a light source, it is important that the light source used to activate a whitening compound or restorative composite be in reasonably close proximity to the tooth surfaces being treated. Also, because the wavelengths most effective for activation of a dental whitening or curing compound may be deleterious to soft tissues, it is desirable to minimize the exposure of a patient's gums, tongue, facial skin and other soft tissues to the curing light source.

In view of these considerations, it is desirable that a light source be supported in a manner that allows its rapid and reliable positioning in proximity to a patient's teeth. Furthermore, a support mechanism to effect this support may be unobtrusive, easily adjusted, and able to provide positioning in multiple degrees of freedom so as to be adaptable to the requirements of patients of various sizes.

A light guide of the present invention includes a tubular inner surface that is disposed about an axial cavity filled with ambient air. An aperture at a proximal end of the light guide is adapted for positioning adjacent to the front aperture of the lamp housing. A further aperture exists at a distal end of the light guide. The light guide also includes at least one formation adapted for inter-engaging the light guide to a light system. The formation may be shaped and configured to mate with and cover at least a portion of a light system.

In one embodiment of the invention, a reference device such as a lip retracting device having at least one formation is adapted to inter-engage with at least one formation in the light guide.

The word formation as used herein in relation to a dental system such as a light system, a light guide, an imaging system, a dental treatment composition, an imaging system, a retracting device, a spacer, or a support system, refers to the portion of the dental system which is adapted to inter-fit with a corresponding portion of an adjoining dental system, component or a subject's mouth. A formation thus includes at least a portion of any of the above listed articles and may be formed or shaped by molding, or the formation may be formed separately and then subsequently assembled with the respective articles.

Suitable inter-engaging formations include tongues and grooves, posts and sockets, swingable hooks and sockets, resilient clips and sockets, clips and protrusions or depressions, tongues or wing-like members and slots, ball and cavity, ball and socket, some of which are more specifically exemplified in detail below. Non-inter-engaging formations include dental trays, imaging film holders, and other features adapted to position any dental treatment or imaging material in a patient's mouth.

FIG. 1 shows a light guide 100 for dentistry applications according to a first embodiment of the invention. As shown, the light guide 100 includes an elliptically tubular member 102 having an axial cavity 104 disposed between a front aperture 106 and a rear aperture 108.

As shown in the illustrated embodiment, a first edge 101 of the tubular member defines a substantially elliptically saddle shaped curve having a convex form in relation to a generally horizontal portion 110 thereof and a concave form in relation to a generally vertical portion 112 thereof. In addition, edge 101 includes first and second formations, for example, substantially horizontal slots 114, 116. According to one embodiment of the invention, the slots 114, 116 are disposed substantially coplanar with respect to one another and are disposed substantially coincident with a major axis of the elliptically saddle shaped curve that defines edge 101.

As shown in the illustrated embodiment, a rim 118 extends radially inwardly from the edge 101 to a second substantially elliptically saddle shaped curved edge 120 (also referred to as the "second edge"). The second edge 120 is disposed in substantially constantly space relation to edge 101, whereby the rim 118 has a substantially uniform radial dimension over the length of edge 101. Edge 120 defines an outer periphery of the front aperture 106.

At the rear end of the embodiment of FIG. 1, a third edge 130 defines another curve that is of an approximately elliptically saddle shape. Edge 130 is substantially concave in form in relation to a generally horizontal portion 132 thereof and is generally convex in form in relation to a generally vertical portion 134 thereof.

According to one embodiment of the invention, curve 130 defines the rear aperture 108 of the light guide.

According to one embodiment of the invention, the light guide does not include a rim adjacent the rear aperture 108.

In a further aspect of the illustrated embodiment, an outer surface 139 of the light guide is disposed between edge 101 and edge 130. An inner surface 136 of the light guide is disposed in substantially uniform spaced relation to outer surface 139 so as to define inward and outward boundaries of the elliptically tubular member 102.

In one embodiment of the invention, outer surface 139 includes a plurality of gripping features 138 adapted to improve the grip of an operator on surface 139 during manipulation of the light guide 100. In the illustrated embodiment, the gripping features 138 have a raised elongated ellipsoid aspect. In another embodiment of the invention of gripping features include a plurality of substantially hemispherical bumps. In still another embodiment of the invention, the gripping features include a plurality of zigzag grooves. One of skill in the art will appreciate that a wide variety of features may be disposed on surface 134, so as to enhance overall gripability of the light guide 100.

Figure 2:
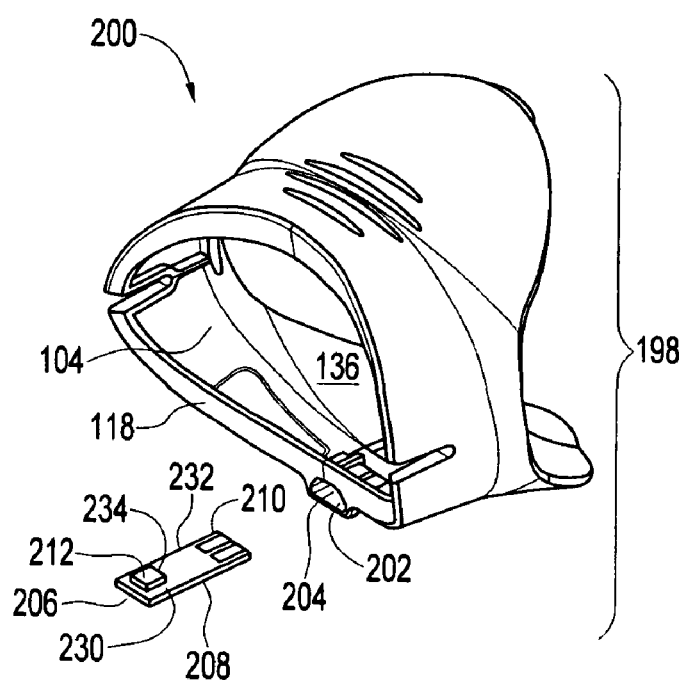
FIG. 2 shows, in perspective view, a light guide including a recording device according to one embodiment of the invention.

FIG. 2 shows a light guide 200 according to another embodiment of the invention. The light guide 200 includes a rim 118 with an aperture 202 in a lower portion thereof. The aperture 202 opens inwardly from a front end of the light guide 200 into an elongated cavity 204 formed, in part, by the inner wall 136 of the light guide. According to one embodiment of the invention, the cavity 204 is adapted to receive a recording device 206 therein.

According to one embodiment of the invention, the recording device 206 includes an assembly having a printed circuit board 208 with an electromechanical contact 210 and a memory integrated circuit 212 disposed thereon. In one aspect, the recording device 206 includes a first side 230 and a second side 232. In the illustrated embodiment, the memory integrated circuit 212 has a rear side 234. Pursuant to one embodiment of the invention, the memory integrated circuit 212 is substantially permanently fixed to the circuit board by, for example, soldering, adhesive bonding, potting or other methods for integrated circuit mounting as are known to those of ordinary skill in the art.

According to one embodiment of the invention, the cavity 204 as defined by a plurality of surfaces, is adapted to support the recording device 206 substantially fixedly with respect to the light guide 200.

In one embodiment of the invention, the recording device 206 is supported in a position such that the electro-mechanical contact 210 is disposed in an elevated and exposed location within axial cavity 104 of the light guide 200.

Figure 3:
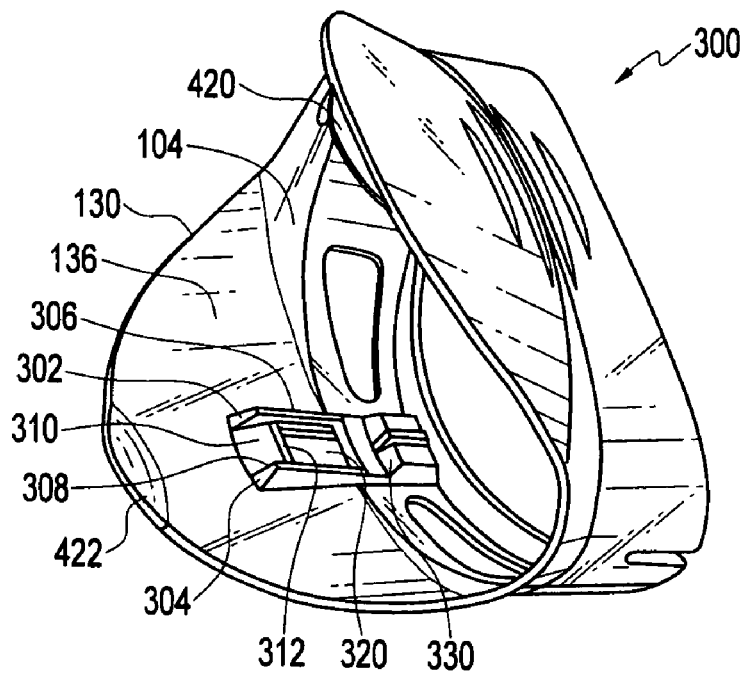
FIG. 3 shows, in posterior perspective view, a light guide according to one embodiment of the invention.

This spatial relationship is shown more clearly in, for example, FIG. 3 which shows a light guide 300 according to one embodiment of the invention in posterior perspective view. The light guide 300 includes, disposed on internal surface 136 a first support member 302 and a second support member 304. Support member 302 includes a first bearing wall 306 and support member 304 includes a second bearing wall 308. A third support member 310 includes a bearing top surface 312.

Turning once again to recording device 206 (as shown in FIG. 2) one sees that recording device 206 is adapted to be received within a region 320 as shown in FIG. 3. When recording device 206 is disposed in region 320, bearing surface 306 is disposed adjacent to and supports edge 230. The bearing surface 308 is disposed adjacent to and supports edge 232 and bearing surface 312 is disposed adjacent to and supports an underside surface (not shown) of recording device 206.

One should note as a further feature of light guide 300, a surface 330 disposed in a generally vertical orientation. A further surface 332 is disposed in substantially parallel spaced relation to surface 330, and forwardly of the same, as shown in FIG. 4.

Figure 4:
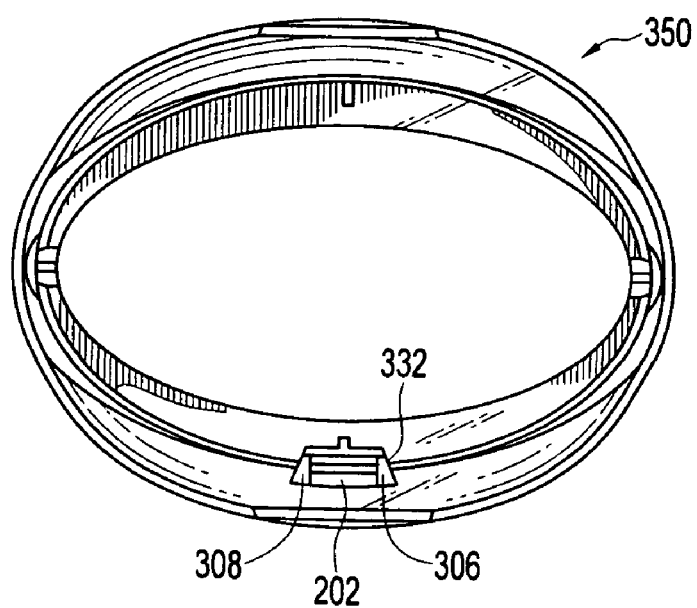
FIG. 4 shows a front elevation of a light guide according to one embodiment of the invention.

Further insight into recording device 206 and its role in the invention is gained by reference to FIG. 4 which shows a light guide 350 according to one embodiment of the invention in anterior elevation. Specifically, FIG. 4 shows the further bearing surface 332 disposed in substantially parallel spaced relation to surface 330 (as shown in FIG. 3) as discussed immediately above. Also shown are aperture 202 (as discussed above in relation to FIG. 2), first bearing wall 308 and second bearing wall 306 (as discussed above in relation to FIG. 3).

One of skill in the art will appreciate that when recording device 206 (as illustrated in FIG. 2) is disposed inwardly of aperture 202, surface 234 of integrated circuit memory device 212 is disposed adjacent to, and supported by bearing surface 332. Furthermore, referring again to FIG. 3, one of skill in the art will appreciate that when recording device 206 is thus disposed, electromechanical contact 210 is disposed in a region adjacent and rearwardly of bearing surface 312 and is exposed within axial cavity 104 from above, below, and from a rearward direction.

Figure 5:
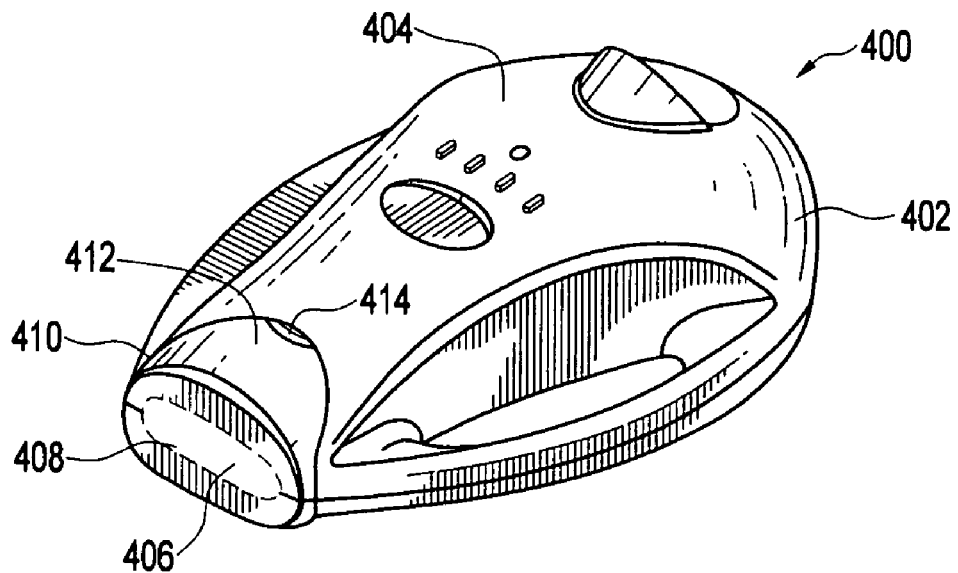
FIG. 5 shows, in perspective view, a dental lamp head adapted to be coupled to a light guide according to one embodiment of the invention.

Turning to FIG. 5, one sees a lamp head 400 according to one embodiment of the invention. As illustrated, the lamp head 400 includes a housing 402 having an outer surface 404. A forward end of the lamp head housing 402 includes an aperture 406 defined by an edge 408. In operation, light is emitted from a light source within the lamp head housing 402 through the aperture 406.

The housing 402 includes an intermediate edge 410 disposed in a curve about aperture 406 in a forward region of the housing 402. Forwardly of the intermediate edge 410, a surface region 412 is recessed in relation to the balance of the housing surface 404.

According to one embodiment of the invention, the lamp head 400 is adapted to removably interface with a light guide 300, such as that indicated, for example, in FIG. 3. Accordingly, surface region 412 is adapted to be disposed adjacent to and to be supported by, internal surface 136 of light guide 300. Likewise, rear edge 130 of light guide 300 is adapted to be disposed adjacent to and supported by edge 410. Thus, the formation of the light guide, for example, the internal surface 136 or edge 410, is shaped and configured to mate with and cover at least a portion of a light system.

In addition, according to one embodiment of the invention, the housing 402 includes at least one formation, such as a top recess 414, and a corresponding bottom recess (not shown). The top recess 414 is adapted to receive a first formation such as a detent projection 420 (as shown in FIG. 3) disposed adjacent edge 130 of light guide 300. In like fashion, the bottom recess is adapted to receive a second formation, such as detent projection 422 as shown in FIG. 3.

According to one embodiment of the invention, the material of the light guide is sufficiently elastic to urge detent projections 420 and 422 into their respective recesses, whereby the light guide is removably retained in position, with axial cavity 104 disposed adjacent to aperture 406 of the lamp head.

According to one embodiment of the invention, when the light guide (e.g., 300) is so disposed, the electromechanical contact 210 (as shown in FIG. 2) is disposed within an electrical plug on the lamp head. This is shown more clearly in FIG. 6, which shows a bottom view of the lamp head 400.

Figure 6:
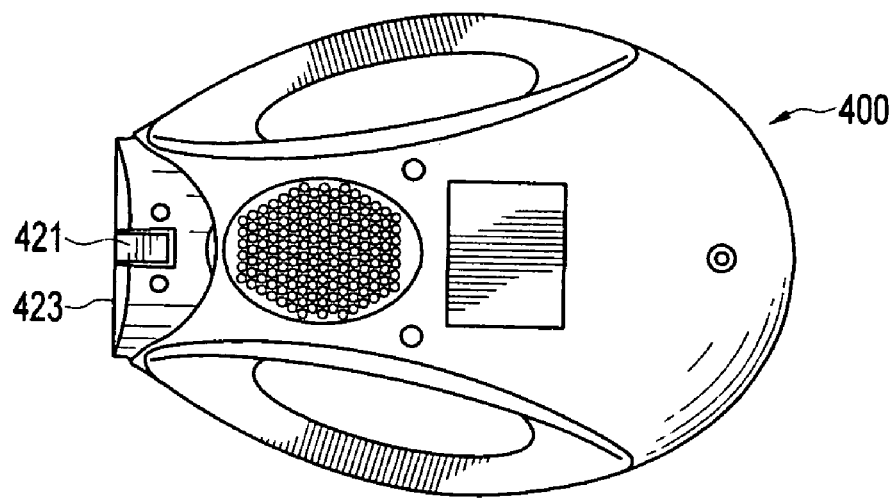
FIG. 6 shows a top view of a dental lamp head adapted to be coupled to a light guide according to one embodiment of the invention.

As shown in FIG. 6, the lamp head 400 includes a further formation, for example, a further recessed region 421 in proximity to the front end 423 of the lamp head 400.

Figure 7:
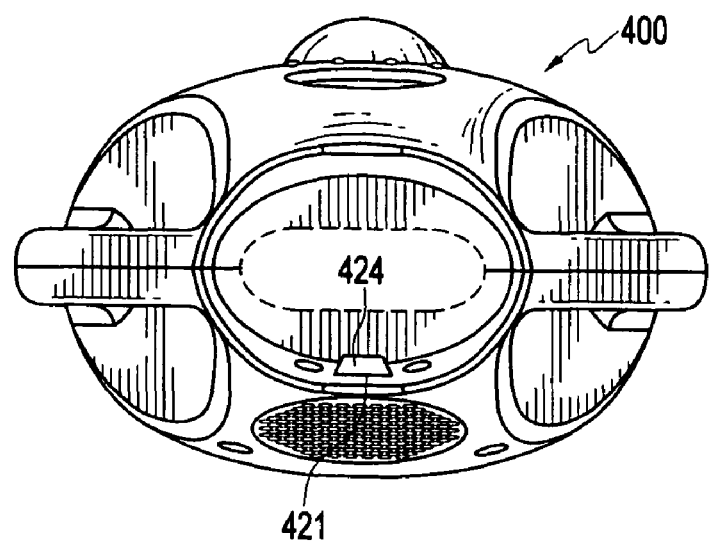
FIG. 7 shows a rear elevation of a dental lamp head adapted to be coupled to a light guide according to one embodiment of the invention.

As shown in FIG. 7, this further recessed region 421 is disposed adjacent to the electrical plug referred to immediately above, which is disposed behind an aperture 424 in the housing 402 of the lamp head 400. The aperture 424 is adapted in size and shape to receive the electromechanical connector 210, as shown in FIG. 2, therethrough.

As mentioned above, the interaction of detent projections 420, 422 and corresponding recesses, e.g., 414 of lamp housing 400 served to Maintain the light guide in position on the lamp housing once it is installed there until it is actively removed.

The lamp housing may also include at least one heat sink, in the proximity of the light source for keeping the light source and the lamp housing cool. The heat sink may be made of any material that has good thermal conductivity, including metal blocks of copper, aluminum or similar. In another embodiment, the cooling system includes heat pipes. In another embodiment, the cooling system includes phase change materials, some embodiments and material are exemplified as is described in U.S. Application No. 60/585,224, "Dental Light Devices With Phase Change Material Filled Heat Sink", filed on Jul. 2, 2004, the contents of which are incorporated herein by reference.

The heat sink may be constructed by hollowing out a thermally conductive material, such as metal, and at least partially filling the void with at least one phase change material prior to capping it to secure the phase change material inside, such that the at least one phase change material is substantially contained or surrounded by a thermally conductive material such as metal normally used in the construction of a conventional heat sink.

Alternatively, the heat sink may be cast or machined from a thermally conductive material, such as metal, to create walls surrounding a bore or void. The bore or void is partially filled with at least one phase change material prior to capping it to secure the material inside.

In one embodiment, the inventive heat sink may be used by itself. In another embodiment, it may be used in addition to a fan, in conjunction with a conventional metal block heat sink or combinations thereof.

Suitable phase change material may include organic materials, inorganic materials and combinations thereof. These materials can undergo substantially reversible phase changes, and can typically go through a large, if not an infinite number of cycles without losing their effectiveness. Organic phase change materials include paraffin waxes, 2, 2-dimethyl-n-docosane ($C_{24}H_{50}$), trimyristin, (($C_{13}H_{27}COO)_3C_3H_3$), and 1,3-methyl pentacosane ($C_{26}H_{54}$). Inorganic materials such as hydrated salts including sodium hydrogen phosphate dodecahydrate ($Na_2HPO_4.12H_2O$), sodium sulfate decahydrate ($Na_2SO_4.10H_2O$), ferric chloride hexahydrate ($FeCl_3.6H_2O$), and TH29 (a hydrated salt having a melting temperature of 29° C., available from TEAP Energy of Wangara, Australia) or metallic alloys, such as Ostalloy 117 or UM47 (available from Umicore Electro-Optic Materials) are also contemplated. Exemplary materials are solids at ambient temperature, having melting points between about 30° C. and about 50° C., more for example, between about 35° C. and about 45° C. Also, the exemplary materials have a high specific heat, for example, at least about 1.7, more for example, at least about 1.9, when they are in the state at ambient temperature. In addition, the phase change materials may, for example, have a specific heat of at least about 1.5, more for example, at least about 1.6, when they are in the state at the elevated temperatures.

The phase change material may also have a high latent heat of fusion for storing significant amounts of heat energy. This latent heat of fusion may be, for example, at least about 30 kJ/kg, more for example, at least about 200 kJ/kg.

Thermal conductivity of the materials is a factor in determining the rate of heat transfer from the thermally conductive casing to the phase change material and vice versa. The thermal conductivity of the phase change material may be, for example, at least about 0.5 W/m° C. in the state at ambient temperature and at least about 0.45 W/m° C. in the state at elevated temperature.

In general, the phase change material may be contained inside a thermally conductive material, such as a metal casing. The casing defines a bore, which may be of any shape, but is for example, generally of a cylindrical or rectangular shape. The metal casing or wall of the bore acts to contain the phase change material, and to also aid in conducting heat to and away from the phase change material. The thinner the wall, the more phase change material can be present in a given size of the heat sink, and the less it contributes to the weight of, for example, the curing light. However, the thinner the wall, the less efficient the heat sink maybe in conducting heat away from the phase change material and the longer it will take to return the phase change material to ambient temperature and its original state, so that it may function as a heat sink again. For example, the wall thickness ranges from about 1 mm to about 2.5 mm, more for example, from about 1 mm to about 1.5 mm.

The casing may also be constructed to have a large surface area. A structure having fins or other features that serve to increase the surface area for heat conduction or convection is desirable, thus a spherical structure, though useful, is not the optimal choice. Such fins or other surface area increasing features may also be incorporated into the bore to increase the contact area between the thermally conductive casing and the phase change material, thus permitting faster more efficient transfer of heat between the thermally conductive casing and the phase change material.

The thermally conductive casing can also provide a good thermal contact for heat transfer from the light source. This may be accomplished with a smooth, thermally conductive surface with a high area of contact. Also, thermal coupling may be achieved with thermally conductive interface materials such as thermal epoxy. Interface materials that are electrically insulating are also useful in isolating the light source from the heat sink in an electrical sense without losing thermal conductivity.

Figure 7A:
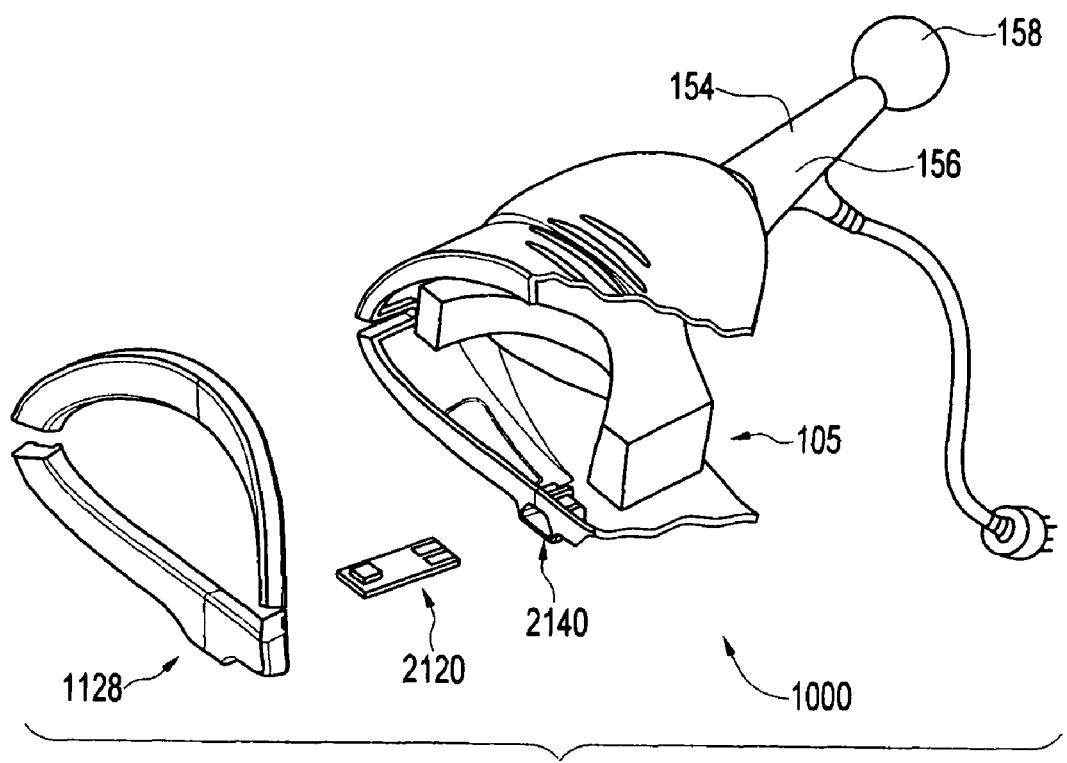
FIG. 7a shows an exploded view of a light guide with an illumination frame.
Figure 7B:
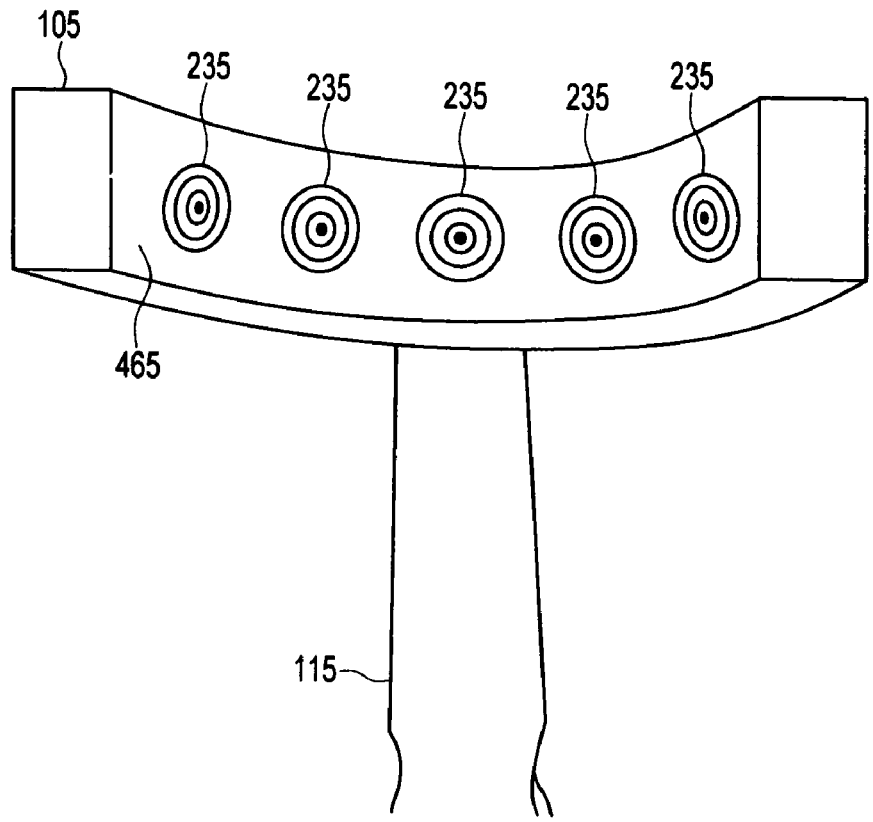
FIGS. 7b and 7c show different embodiments of an illumination frames.
Figure 7C:
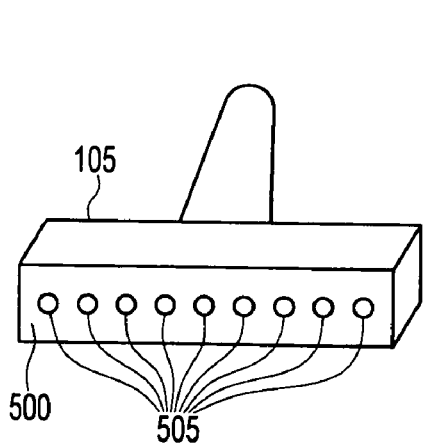
Figure 9:
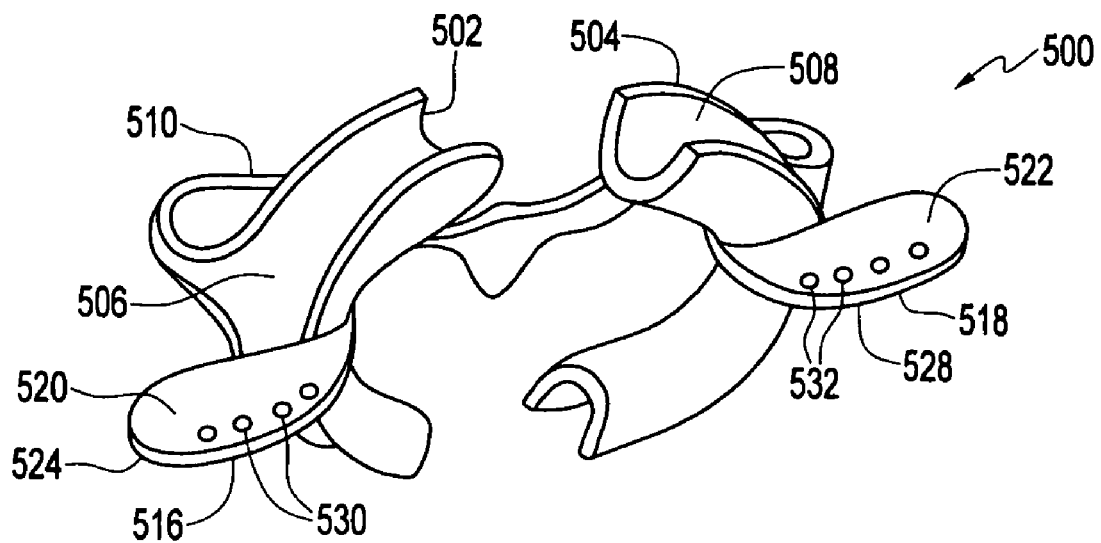
FIG. 9 shows, in perspective view, a lip retractor adapted to be coupled to a light guide according to one embodiment of the invention.

FIG. 7a shows another example of a lamp system, for example, an illumination frame 105, having at least one light source arranged in a geometrical arrangement, such as shown in FIGS. 7b and 7c. The illumination frame 105 may be attached to or disposed inside a light guide 106, having formations, such as slots for engaging with a reference device, such as a lip retracting device 500, as shown in FIG. 9, also having formations, such as wing-like members 520, 522, for positioning the illumination frame 105 with respect to a subject. An elastic member 1128 may be disposed between the patient and the light guide 106. The elastic member 1128 serves to cushion the interface between the patient and the light guide 106, absorbing shocks which might otherwise be painful or uncomfortable.

In one embodiment, the illumination frame 105 has a plurality of light sources 235 that are substantially evenly spaced across the surface of the front of the illumination frame 465, as exemplified in FIG. 7a. Other embodiments of the invention have different arrangements of light sources 235 across the front 465. For example, instead of being evenly spaced, the light sources may be staggered. The present invention is not limited to the number and arrangement of light sources 235 shown here.

FIG. 7c shows another embodiment of the illumination frame 105 having a generally rectangular shape and a substantially flat front surface 500 with a plurality of light sources 505 arranged along the front side 500.

The illumination frames may include formations adapted to coincide with the formations in the light guide for coupling with the wing-like members of a lip retracting device.

Figure 7D:
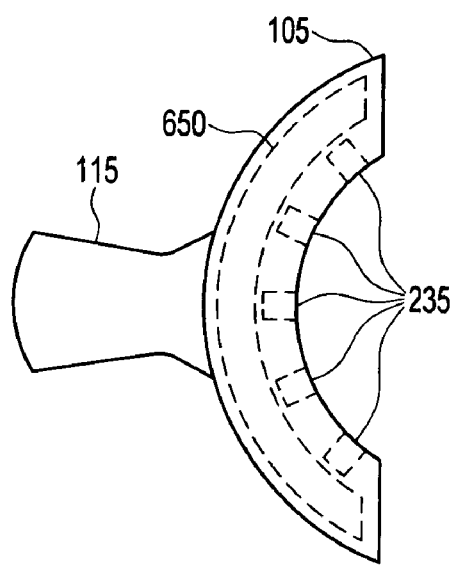
FIG. 7d shows an embodiment of an illumination frame having a heat sink.

FIG. 7d is a top view of an illumination frame 105 including a heat sink according to one embodiment of the invention. The illumination frame 105 has a plurality of light sources 235, having a heat sink 650 coupled to their ballasts (or, base). The heat sink 650 may be made of any material as described above, including a phase change material. The heat sink may also be of any shape.

In the illumination system with multiple light sources, the light sources may be collectively powered or individually powered. If individually powered, each of the individual light sources may be turned on or off separately, as desired. This is especially useful for a curing or imaging process, where only one or two teeth may be undergoing treatment or being examined.

Figure 8:
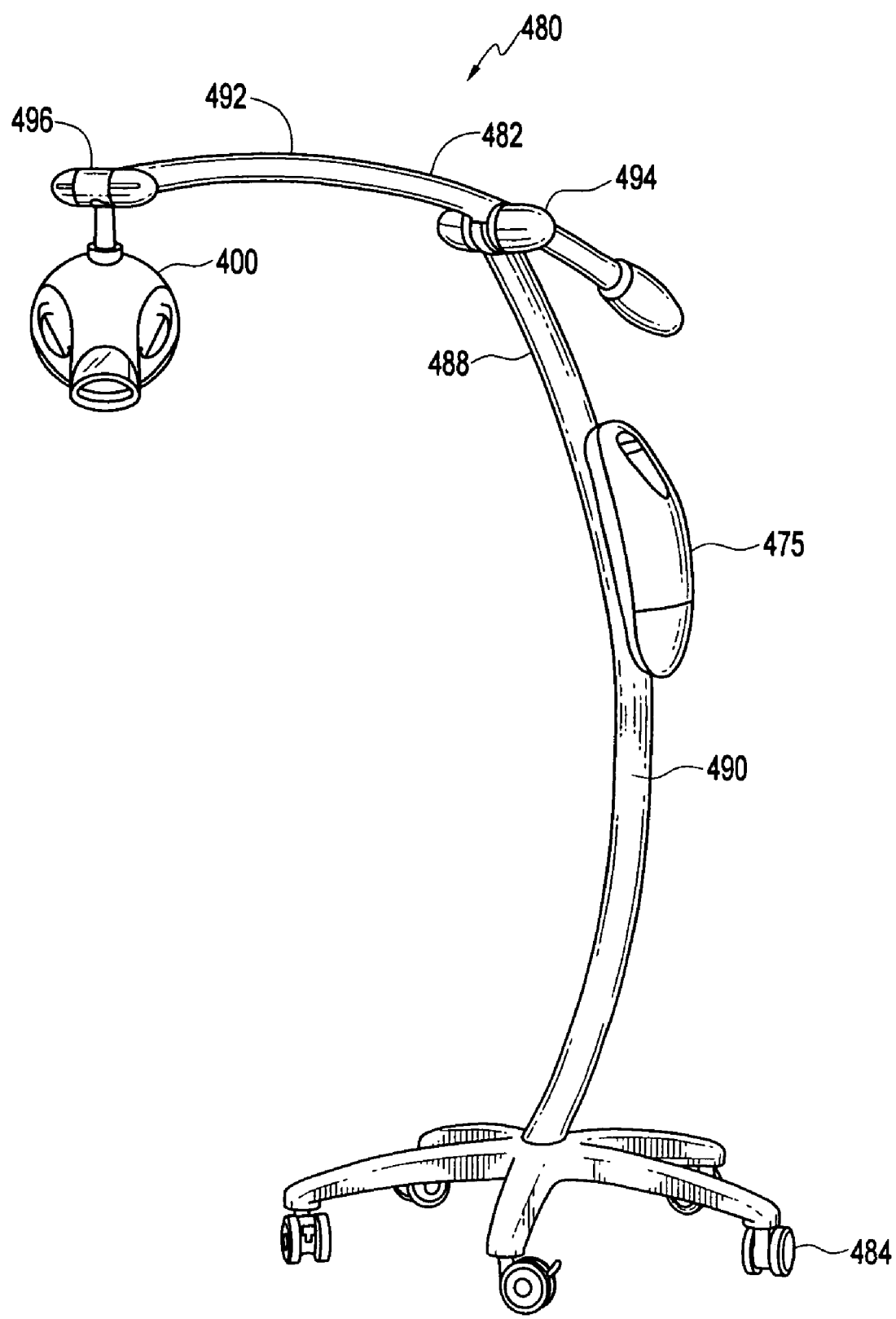
FIG. 8 shows, in perspective view, a dental lamp system including a light guide according to one embodiment of the invention.

In FIG. 8, an exemplary lamp system for dentistry applications 480 including a lamp head 400 supported by a support structure 482 is shown. The support structure 482 includes, in the exemplary embodiment shown, a plurality of caster wheels 484 for mobility and an articulated support member 488, including a mast 490, a boom 492 and an articulating joint 494. In addition, in the illustrated embodiment, the lamp head 400 is coupled to the mast 492 by a ball and socket joint 496 adapted to allow adjustment of a position and orientation of the lamp head through additional degrees of freedom.

According to one embodiment of the invention, it is desirable to position and orient the lamp head in substantially fixed relation with respect to a target of the lamp's illumination, such as a tooth. For example, during a dental whitening process, it is desirable to maintain the distance and orientation between illumination source fixedly contained within the lamp head and a target tooth bearing a whitening compound, so as to maintain a substantially uniform illumination intensity over the target tooth both spatially and during a whitening procedure duration, for example.

An illumination frame may also be supported by a similar structure as shown in FIG. 8.

The lamp housing and head may be made of any polymeric material, for example, a polymer that can be molded or cast; or a metal or metallic alloy. Suitable polymers include polyethylene, polypropylene, polybutylene, polystyrene, polyester, acrylic polymers, polyvinylchloride, polyamide, or polyetherimide like ULTEM®; a polymeric alloy such as Xenoy® resin, which is a composite of polycarbonate and polybutyleneterephthalate or Lexan® plastic, which is a copolymer of polycarbonate and isophthalate terephthalate resorcinol resin (all available from GE Plastics), liquid crystal polymers, such as an aromatic polyester or an aromatic polyester amide containing, as a constituent, at least one compound selected from the group consisting of an aromatic hydroxycarboxylic acid (such as hydroxybenzoate (rigid monomer), hydroxynaphthoate (flexible monomer), an aromatic hydroxyamine and an aromatic diamine, (exemplified in U.S. Pat. Nos. 6,242,063, 6,274,242, 6,643,552 and 6,797,198, the contents of which are incorporated herein by reference), polyesterimide anhydrides with terminal anhydride group or lateral anhydrides (exemplified in U.S. Pat. No. 6,730,377, the content of which is incorporated herein by reference) or combinations thereof.

In addition, any polymeric composite such as engineering prepregs or composites, which are polymers filled with pigments, carbon particles, silica, glass fibers, conductive particles such as metal particles or conductive polymers, or mixtures thereof may also be used. For example, a blend of polycarbonate and ABS (Acrylonitrile Butadiene Styrene) may be used for the lamp housing and head.

Generally, polymeric materials or composites having high temperature resistance are suitable.

Suitable metal or metallic alloys may include stainless steel; aluminum; an alloy such as Ni/Ti alloy; any amorphous metals including those available from Liquid Metal, Inc. or similar ones, such as those described in U.S. Pat. No. 6,682,611, and U.S. Patent Application No. 2004/0121283, the entire contents of which are incorporated herein by reference.

A liquid crystal polymer or a cholesteric liquid crystal polymer, one that can reflect rather than transmit light energy, may be used, either as a coating or as the main ingredient of the housing 104 and/or lamp head 102, to minimize escape of light energy, as described, for example, in U.S. Pat. Nos.

4,293,435, 5,332,522, 6,043,861, 6,046,791, 6,573,963, and 6,836,314, the contents of which are incorporated herein by reference.

According to one embodiment, the structure of the light guide, e.g., 300 includes a UV-inhibiting material in order to protect the patient's skin from ultra-violet light exposure. The light guide may be made of similar material as that of the lamp housing and lamp head as described above. Also, biodegradable or biocompostable polyesters such as a polylactic acid resin (comprising L-lactic acid and D-lactic acid) and polyglycolic acid (PGA); polyhydroxyvalerate/hydroxybutyrate resin (PHBV) (copolymer of 3-hydroxy butyric acid and 3-hydroxy pentanoic acid (3-hydroxy valeric acid) and polyhydroxyalkanoate (PHA) copolymers; and polyester/urethane resin are also suitable, especially if designed for single-use.

Additionally, like the lamp housing and the lamp head, a cholsteric liquid crystal polymer, one that can reflect rather than transmit light energy, may be used, either as a coating or as the main ingredient of the light guide to minimize escape of light energy, as described above.

FIG. 9 shows a reference device for maintaining the lamp head in substantially fixed relation with respect to a target tooth. The reference device of FIG. 9 is a lip retractor according to one embodiment of the invention. As seen in the configuration, the lip retractor includes first 502 and second 504, semicircular "U"-shaped channels adapted to receive the lips of a dental patient adjacent to respected internal surfaces 506, 508 thereof.

A support member 510 is mutually coupled to the "U"-shaped channels 502, 504 and adapted to support the "U"-shaped channels 502, 504 in substantially fixed spatial relation with respect to one another. According to one embodiment of the invention (not shown) the support member 510 also supports a tongue-retainer cup adapted to retain a patient's tongue and shield the same from incident illumination.

According to one embodiment of the invention, a pair of formations such as interface wing-like members 516, 518 are coupled to the "U"-shaped channels 502, 504 respectively. According to one embodiment of the invention, the interface wing-like members each include a respective upper surface 520, 522 and a respective lower surface 524, 528. According to one embodiment of the invention, upper surface 520 is disposed in substantially parallel spaced relation to lower surface 524 and upper surface 522 is disposed in substantially parallel space relation to lower surface 528.

Pursuant to one embodiment of the invention, a plurality of ticks 530, 532 on the upper surfaces 520, 522 can be used for providing visual alignment in the horizontal axis.

According to one embodiment of the invention, interface wings 516 and 518 are adapted to be received within slots 114 and 116 (as shown in FIG. 1) respectively. By pressing the lip retractor 500 toward the front edge 101 (as shown in FIG. 1) of light guide 100, the interface wings 516 and 518 are urged into slots 114 and 116, whereby the orientation and position of the lip retractor 500 with respect to the light guide 100 is substantially fixed. Consequently, the wing-like members of the retracting device 500 may effectively serve to couple the head and teeth of a patient and maintain in substantially fixed position with respect to a light source disposed within a lamp head as shown, for example in FIG. 5.

The lip retracting device may be made by injection molding or casting a thermoplastic material such as polypropylene, polyethylene, polystyrene, polyester, polycarbonate or the like. The lip retracting device 10 may also be made out of biocompostable or biodegradable polymers including those materials mentioned above in relationship to the light guide.

More for example, the lip retracting device 10 may be made by injection molding polypropylene and may be a smooth and transparent finish. In another embodiment, the device may be opaque and colored, including white color.

Figure 10:
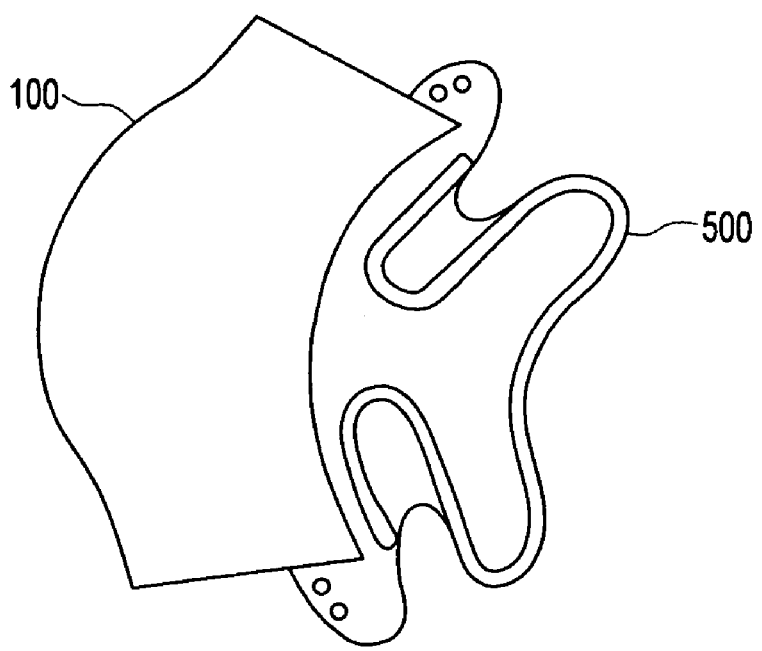
FIG. 10 shows a top view of a light guide and a lip retractor are courting to one embodiment of the invention.

FIG. 10 shows a top view of light guide 100 coupled to a lip retractor 500 according to one embodiment of the invention. As seen in FIG. 10, the configuration of the light guide 100 and lip retractor 500 are adapted to maintain these two components in a substantially constant axial relationship to one another. One skilled in the art will appreciate that, by inserting a first and second stop in respect to holes in the wings of the lip retractor 500, the distance at which the lip retractor 500 is able to advance towards the light guide 100 may be adjusted.

Figure 11:
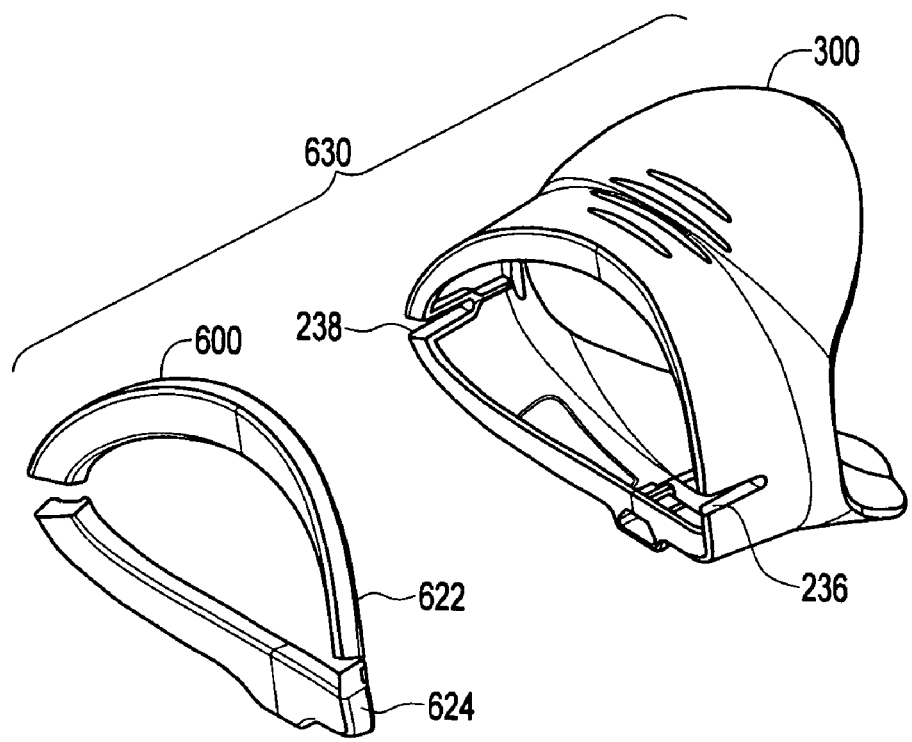
FIG. 11 shows, in exploded perspective view, a light guide including a flexible cushion according to one embodiment of the invention.

According to one embodiment of the invention, as shown in FIG. 11 an elastic member 600 is disposed between the patient and the light guide 300. The elastic member 600 serves to cushion the interface between the patient and the light guide, absorbing shocks which might otherwise be painful or uncomfortable.

In one embodiment the elastic member 600 is for example made from polymer foam or from rubber and is attached to the light guide 300 by adhesive. In the present embodiment, the elastic member 600 is made in two pieces, an upper portion 622 and a lower portion 624, extending the slots 236, 238 of the light guide so as to accommodate wing members of an exemplary lip retracting device.

The elastic member 600 may be made of any open-cell or closed-cell foam, natural or synthetic rubber. Synthetic rubbers may be, for example, elastomeric materials and may include, but not limited to, various copolymers or block copolymers(Kratons®) available from Kraton Polymers such as styrene-butadiene rubber or styrene isoprene rubber, EPDM (ethylene propylene diene monomer) rubber, nitrile (acrylonitrile butadiene) rubber, latex rubber and the like. Foam materials may be closed cell foams or open cell foams, and may include, but is not limited to, a polyolefin foam such as a polyethylene foam, a polypropylene foam, and a polybutylene foam; a polystyrene foam; a polyurethane foam; any elastomeric foam made from any elastomeric or rubber material mentioned above; or any biodegradable or biocompostable polyesters mentioned above in connection with the light guide itself.

The elastic protector pieces 622, 624 may be attached to the light guide by means of heat sealing or an adhesive. Suitable adhesives may include, but are not limited to, structure adhesives, hot melt adhesives, pressure-sensitive adhesives, reactive adhesives or the like. Alternatively, suitable adhesives may be acrylic-based, polyurethane-based, epoxy-based, cyanoacrylate based, polyamide-based, styrene copolymer-based, polyolefin-based or similar. Further, the elastic protector pieces 622, 624 may be integrally molded onto the light guide. Still further, the elastic protector may be in one pece to be attached or integrally molded onto the light guide.

Figure 12:
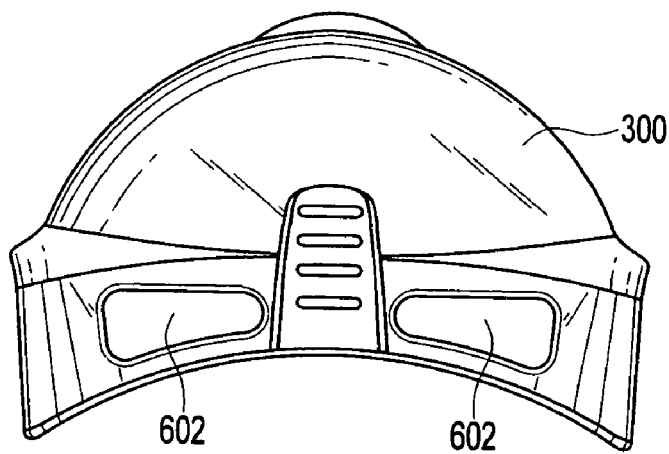
FIG. 12 shows a top view of a light guide according to one embodiment of the invention.

According to another embodiment of the invention, as shown in FIG. 12, a light guide 300 includes one or more ventilation holes 602 adapted to allow a patient to breathe more easily during use of the light guide apparatus.

The air vents 602 are configured to pass air but to prevent light leakage out of the light guide 300.

According to one embodiment of the invention, a light guide 200 (as shown in FIG. 2) may be intended to be a single-use item, or a one-patient use item, used for one dental treatment and then discarded.

A single-use or one-patient use light guide may include materials that are non-sterilizable and/or non-autoclavable. These materials may be used for constructing a substantial portion or an insubstantial portion. For example, the foam pad or its attachment means may be constructed of one-use material, while the body of the light guide may be made of sterilizable or autoclavable material. For another example, the body of the light guide may also be made of one-use material.

The biocompostable or biodegradable polymers, including those mentioned above, are particularly suited for single use or one-patient use light guides.

Additionally, and as discussed above, the light guide 300 may further include a memory integrated circuit 212 disposed within a space 204 molded into the underside of the light guide 300. The memory integrated circuit 212 stores a record of a duration of use signal indicating how long the particular light guide has been in use. The light guide memory integrated circuit 212 is part of a system for ensuring that the light guide 300 is not improperly reused.

In operation, the light guide 300 is attached to the lamp head housing 402. The light guide 300 has both a mechanical attachment mechanism (slots 114, 116, as shown in FIG. 1, for receiving the wings 516, 518, as shown in FIG. 9) and an electrical contact as described above between the recording device 208 and the electronics in the lamp head housing. The electrical contact 210 mates with, for example, a conductive plug in the lamp head forming an electro-mechanical connection that enables signaling between the light guide recording device 208 and electronics in the lamp head housing.

The light guide 300 may be aligned with the patient's mouth using the positionability of the lamp system 480 (as shown in FIG. 8) and, for example, a whitening treatment composition is administered. A signaling device within lamp head, or within the power pack, records the duration of use of light guide usage onto the recording device. When a light guide usage limit is reached, the lamp system precludes activation of the light source in the lamp head housing 204 and the light guide 300 is replaced in order to operate the lamp system.

In an alternative embodiment of the light guide 300, no elastic member 600 is used to interface between the light guide 300 and the patient. In further alternative embodiments of the light guide 300, the contact between the light guide recording device 208 and electronics in the lamp head is a magnetic contact. Alternatively, the recording device 208 may communicate with the lamp head through infrared radiation or through wireless radio signals or through light from the visible portion of the electromagnetic spectrum or through acoustic transmission.

Once the lamp system 480 (as shown in FIG. 8) is positioned with respect to the patient, the operator aligns the light guide 300 with the patient's mouth. The light guide 300 may be set to a wide range of positions through the wide range of motion of both the boom 492 with respect to the mast 490 and the lamp head 400 with respect to the boom 492. The light guide 300 is shaped and configured to mate with a lip retracting device, such as shown in FIG. 9. The lip retracting device may be worn by the patient thereby providing a substantially precise alignment with the patient's mouth.

FIG. 13 shows an assembly relationship between the ball joint 902 of lamp head 1102, a light guide 1104, and a lip retractor device 1138 according to one embodiment of the invention. As shown in FIG. 13, a pivot mount 906 is coupled between the lamp head 1102 and the ball joint 902. The ball joint allows the lamp head to be swiveled in space such that an optical axis of the lamp is aligned with the target teeth of a dental subject.

A light guide 1104 is adapted to be coupled to an anterior end of the lamp head 1102. In one embodiment, the light guide 1104 includes an inner surface region 1122 that is adapted to be held in proximity to an outer surface region 1124 of the lamp head 1102. According to one embodiment of the invention, a projecting member, or bump, on inner surface 1122 is adapted to be urged into a recessed region 1126 of outer surface region 1124.

In one embodiment of the invention, the light guide 1104 includes an elastically compressible cushion 1128 at an anterior edge thereof. The elastically compressible cushion 1128 serves to soften an interface between a dental whitening process subject (not shown) and the light guide, as noted above.

In a further aspect of the invention, as shown in the illustrated embodiment, the light guide 1104 includes first and second slots 1130 and 1132. These slots are adapted to receive projecting wings 1134, 1136 of a lip retracting device 1138 so as to stabilize a relationship between the dental subject and the lamp head 1102.

The lip retracting device 1138 includes channels 1140, 1142 adapted to support the lips of a dental whitening subject during the whitening process, and a resilient or elastic member 1144. The elastic or resilient member 1144 is coupled to the channels 1140, 1142 and adapted to urge the channels outwardly towards the lips, so as to couple the subject undergoing the dental process to the lip retracting device.

When the subject is coupled to the lip retracting device 1138, and the lip retracting device is coupled to the light guide 1104 by the insertion of wing-like members 1134, 1136 in the respective slots 1130, 1132 in the light guide 1104, the subject is spatially stabilized with respect to the lamp head 1102. In this way the support structure serves to support the lamp head in a substantially stable spatial relationship to the whitening subject.

The use of light guides of the present invention may promote less air circulation between the patient's mouth and the ambient surroundings during treatment. With less air circulation inside the mouth, there may be less evaporation of any treatment composition or whitening composition, which may lead to less dehydration of the mouth. Without wishing to be bound by a theory, it is surmised that since dehydration may lead to increased sensitivity, less dehydration of the mouth may lead to decreased dehydration of the teeth and thus decreased teeth sensitivity during and after treatment. Thus, the use of a light guide during bleaching process may potentially be advantageous.

Figure 13A:
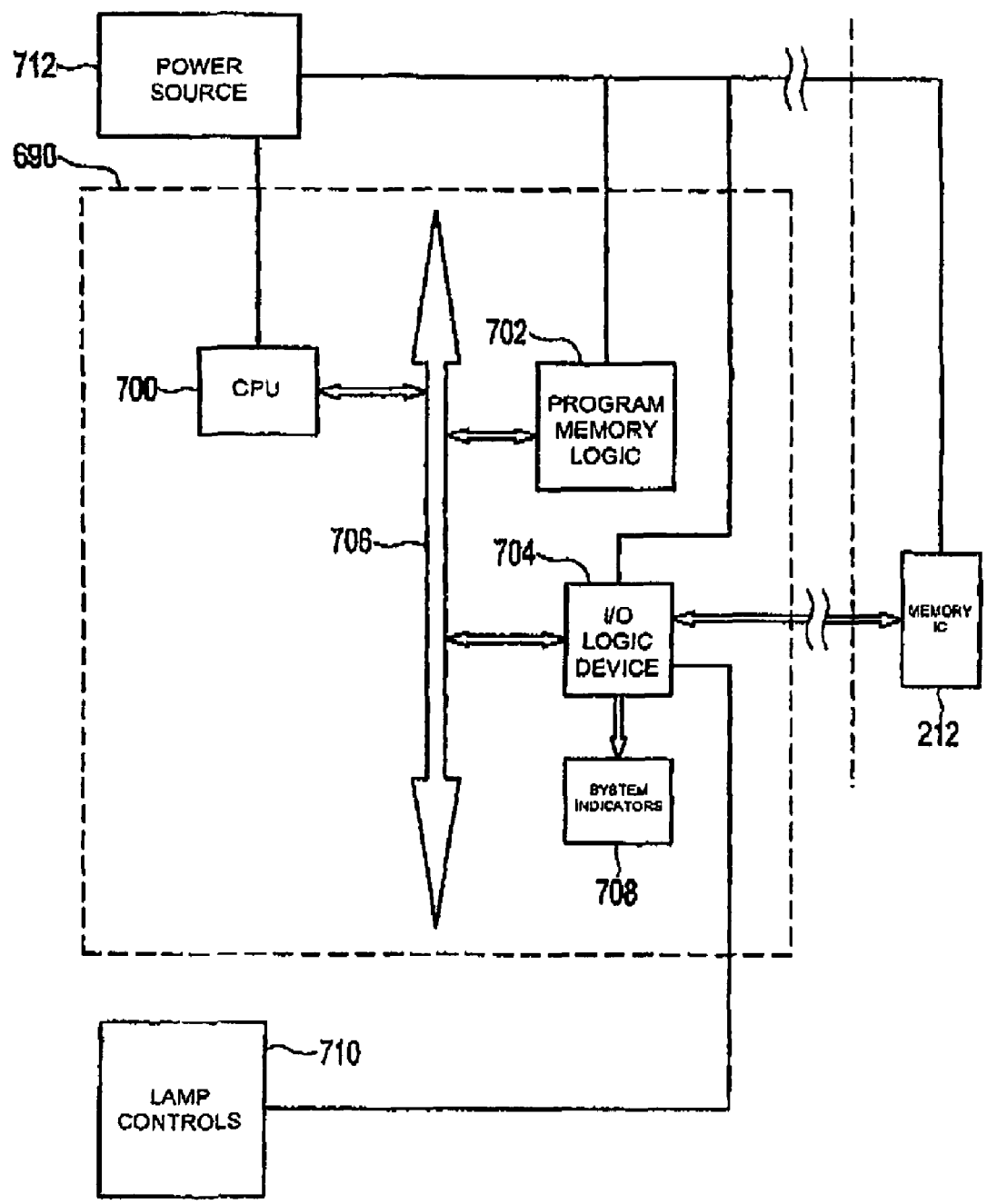
FIG. 13a shows, in block diagram form, a control system according to one embodiment of the invention.

FIG. 13*a* is a block diagram of an embodiment of the control system 690 of the lamp system 480 of the present invention. In one embodiment, the microelectronics of the control system 690 are located in the lamp head 400. In another embodiment, the microelectronics of the control system 690 are located in the power pack 475. Other locations for the control system electronics are possible within the scope of the invention.

The control system 690 includes a CPU 700, program memory logic 702, an I/O logic device 704, a data bus 706 and system indicators 708. The CPU 700, program memory logic 702, and the I/O logic device 704 are connected to the data bus 706. The I/O logic device 704 is further connected to system indicators 708. In one embodiment of the invention, the I/O logic device 704 further includes device drivers. The I/O logic device 704 is further connected to the memory integrated circuit 212 located on the light guide (shown in FIG. 10). Lamp controls 710 are connected to the I/O device 704. A power source 712 provides power to the CPU 700, program memory logic 702, the I/O logic device 704 and the memory integrated circuit 212.

The CPU 700, program memory logic 702 and the I/O logic device 704 are for example, microelectronic devices, located in the lamp head 400. In an alternative embodiment of the invention, the lamp controls 710 and power 712 are also located in the lamp head 400. In an alternative embodiment of the invention, the CPU 700, program memory logic 702, I/O logic device 704, lamp controls 710, and power 712 are, for example, located in the power pack 475. The lamp controls 710 are, for example, a transistor device or electronic or electromechanical relay device for controlling the on/off function of the lamp system 480. The system indicators 708 are, for example, the lighted indicators on the lamp head 400.

Figure 14:
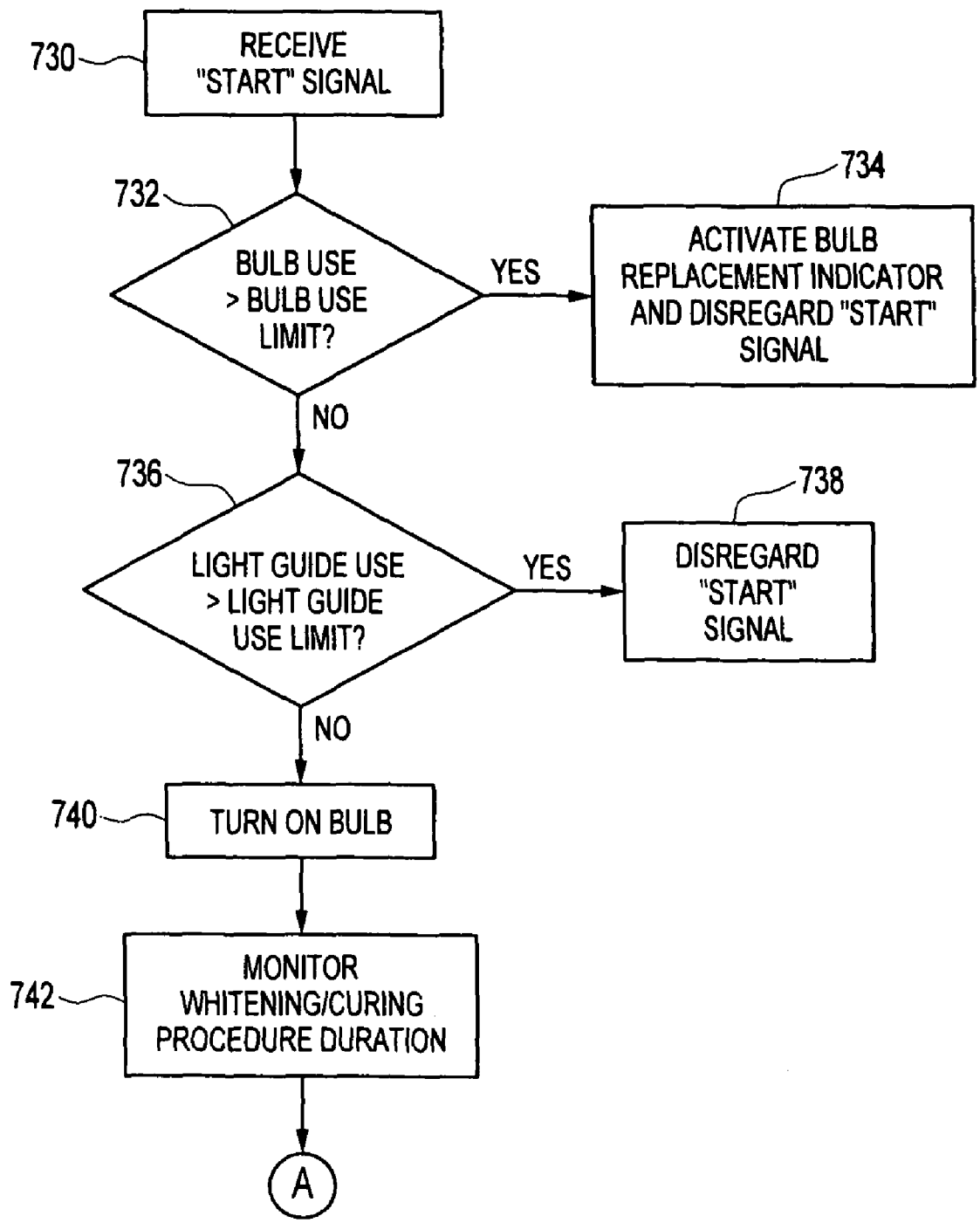
FIGS. 14 and 15 show, in flowchart form, a method of monitoring system operation according to one embodiment of the invention.

FIG. 14 is a flow chart showing one embodiment of the start process of the lamp system 480 that is executed by the control system 690 illustrated in FIG. 13.

At step 730, the control system 690 receives a "start" signal from the lamp controls 710. The "start" signal activates an initializing process that includes determining whether a bulb in the lamp head 400 and light guide 300 have reached their usage limits. The control system 690 stores a bulb usage limit, a light guide usage limit, and a whitening/curing procedure time limit. According to one embodiment of the invention, the duration between the start of a procedure and the procedure time limit is divided by the control system 690 into preselected time intervals.

At step 732, the control system 690 checks whether the bulb has been used longer than the bulb usage limit stored in the control system 690. According to one embodiment of the invention, the bulb usage limit is, for example, 100 hours. According to a further embodiment of the invention, the bulb usage limit may be modified subsequent to an original use of the system by a customer such as a dental practitioner. For example, a light source usage limit value may be modified when a lamp head is returned to a service facility for replacement of a light source. The control system 690 monitors the time that the light source in the lamp head 400 is on and adds this value to the amount of time accumulated from previous treatment procedures, if any. When the "start" signal is received from the lamp controls 710, the control system 690 compares the accumulated light source on time with the light source usage limit. If the light source usage limit has been exceeded, the control system 690 proceeds to step 734. If the light source usage limit has not been exceeded, the control system 690 proceeds to step 736.

At step 734, the control system 690 activates the light source replacement indicator 152 in the lamp head 400. The control system 690 also disregards the "start" signal with regard to turning on the light source. In other words, the control system 690 does not allow the lamp system to operate if the control system 690 determines that the light source lifetime has been exceeded. The control system 690 is reset when the light source is replaced.

At step 736, the control system 690 determines whether the light guide usage has exceeded the light guide usage limit stored in the control system 690. The light guide usage limit is typically the amount of time of a single whitening or curing treatment. The light guide usage limit is, for example, sixty minutes. The control system 690, as mentioned above in step 732, monitors the time that the light source is on. The control system 690 writes the amount of time that the light source has been on since the beginning of a treatment procedure to a recording device on the light guide 300. The recording device is, for example, a memory integrated circuit 212. When the "start" signal is received from the lamp controls 710, the control system 690 compares the light source "on" time stored on the recording device in the light guide 300 with the light guide use limit stored by the control system 690. If the light guide use limit has been exceeded, the control system 690 proceeds to step 738. If the light guide use limit has not been exceeded, the control system 690 proceeds to step 740.

At step 738, the control system 690 disregards the "start" signal with regard to turning the light source on. That is, the control system 690 does not allow the lamp system to operate if the light guide lifetime has expired. This portion of the control system 690 acts to prevent the light guide from being reused. The light guide 300 is intended to be a single-use device to be discarded after each whitening or curing treatment.

At step 740, the control system 690 starts the lamp (i.e. turns on the light source).

At step 742, the control system 690 monitors the whitening or curing treatment procedure time. In this step, the control system 690 monitors the time that the light source is on. The monitoring procedure of the control system 690 is described below with regard to FIG. 15.

Figure 15:
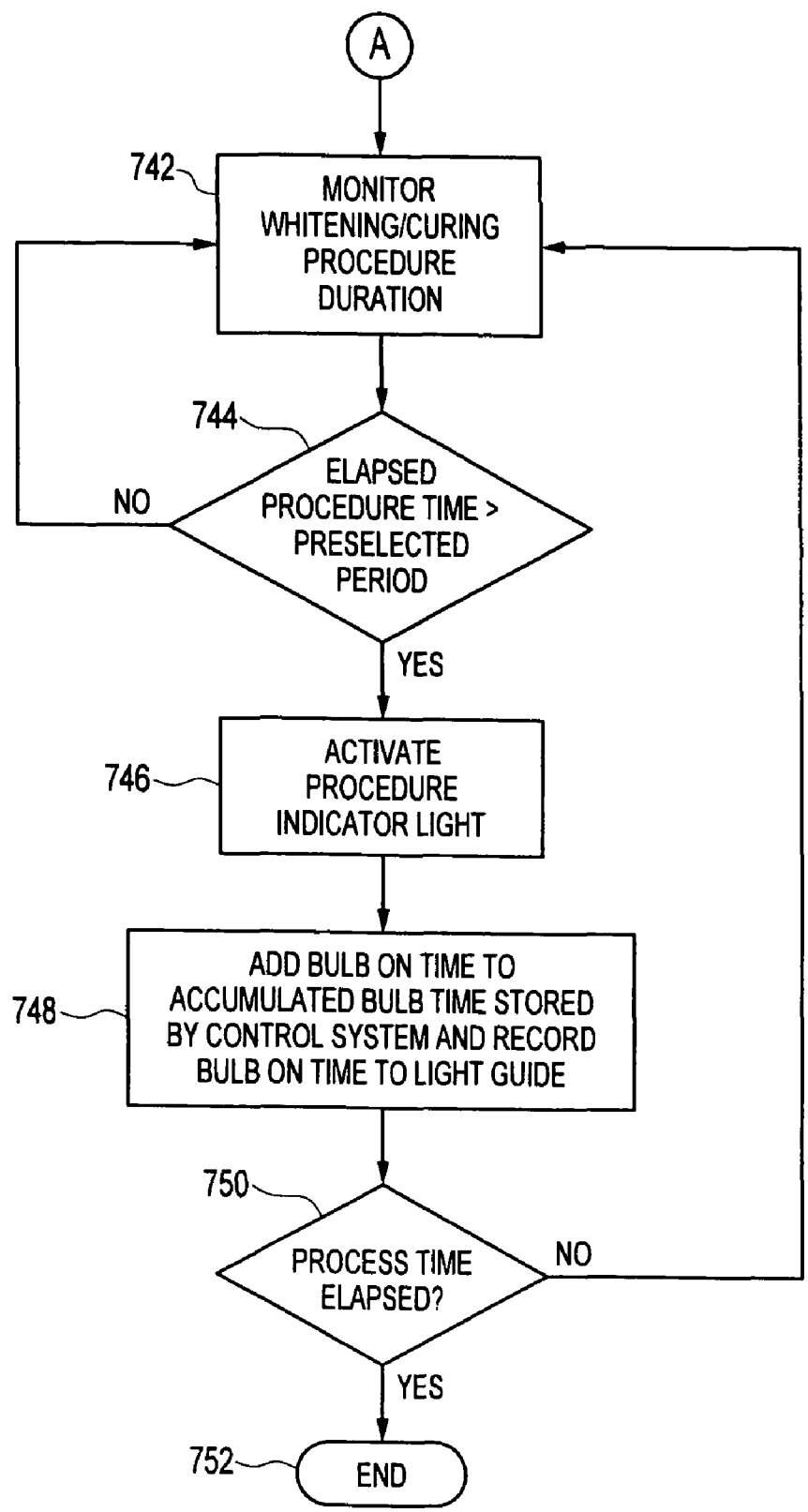

FIG. 15 is a flow chart showing one embodiment of the monitoring process of the lamp system 480 that is executed by the control system 690 illustrated in FIG. 13a.

At step 742, the control system 690 monitors the duration of the whitening or curing treatment, that is, the control system 690 monitors the light source "on" time.

At step 744, the control system 690 determines whether the elapsed procedure time has exceeded a preselected time period. Here, the preselected time period is some portion of the overall treatment time such as one quarter of the total treatment time. If the elapsed procedure time has not exceed the preselected time period, the control system 690 continues to monitor the treatment duration (step 742). If the elapsed procedure time does exceed the preselected time period, then the control system 690 proceeds to step 746.

At step 746, the control system 690 activates a procedure indicator light, for example one of the lighted indicators on the lamp head 400. In one embodiment, the control system 690 activates another lighted indicator as each treatment portion time elapses so that if, for example, there are four lighted indicators, all four are lit at the end of the treatment procedure. In another embodiment, there is a single lighted indicator to indicate the time progression of the treatment. In this embodiment, the light indicator has varying flash rates to indicate the how much time has elapsed since the start of treatment. The control system 690 then proceeds to step 748.

At step 748, the control system 690 adds the time that the light source has been on to the accumulated time that the control system 690 has stored from previous treatment procedures, if any. The control system 690 also writes the time that the light source has been on to the light guide recording device, such as the memory integrated circuit 212. The control system 690 then proceeds to step 750.

At step 750, the control system 690 determines whether the overall process time has elapsed. The overall process time is the time duration of the whitening or curing treatment. If the overall process time has not elapsed, the control system 690 returns to step 742, monitoring the whitening/curing duration. If the overall process time has elapsed, the control system 690 proceeds to step 752.

At step 752, the duration of the whitening/curing treatment has elapsed and the control system 690 turns off the light source.

Alternatively, in another embodiment of the invention, a control system having a built-in voice alert system for alerting a dental professional of the time, or stage, in a dental procedure may be included. The control system may also include a headphone or other private listening device, for example, so that only the dental professional will receive the voice alert. In one aspect, the private listening device may be a wireless listening device such as a wireless radio channeling device or an infrared channeling device.

In one embodiment, a dental light system includes a built-in electronic voice alerting system to alert the dental professional of the completion of a dental procedure.

In one aspect, the electronic voice alerting system may utilize an electronic voice generating circuit technology, similar to the technology used in electronic devices such as toys, cell phones, automobiles and other consumer electronics, but with novel message content that is directed to dental applications.

In still another embodiment, a dental illumination system includes an audible electronic voice alert system having a novel approach to tracking time during the above mentioned dental procedures and other similar dental procedures. This audible electronic voice alert system uses an electronic device with prerecorded time interval statements stored in the device.

According to one embodiment, the alert system, in addition to having the lighted indicators mentioned above, is also adapted to play a recorded voice that is generated when an electronic timer circuit is programmed to play the appropriate electronic voice count alert through an audio speaker in the device. In one aspect, the message played may include time intervals, and may be programmed and in some embodiments, re-programmed.

In a further embodiment, a dental lamp system having an electronic timer device is controlled by a microprocessor with an internal clock. The microprocessor receives a signal so as to know when a lamp is first turned on. At predefined intervals of, for example, five seconds, the electronic voice chip sends a recorded audio signal to a speaker to announce elapsed and/or remaining time to the user. In one embodiment of the invention, the speaker is disposed within the light source. This process may be programmed to continue and announce the ten second intervals when the voice chip releases a different recorded audio signal of "ten seconds". Various time increments and corresponding audio signals can be programmed or selected according to the requirements of a particular dental procedure.

In yet a further embodiment of the invention, a dental lamp system includes a prerecorded audio stream that may be configured to play a unique alert message at the end of a procedure. The pre-recorded audio signal can include a message such as "procedure complete", "end of a first cycle" when used in chairside whitening procedures, or similar phrase. Additionally, the system may be configured to give instruction to the dental professional at certain times during the procedure. Exemplary messages may include prerecorded audio streams announcing, "the procedure is almost complete", "please plan for the next step in the whitening process", and "whitening lamp warm up cycle complete." Numerous and various such voice alerts are possible and are intended to be within the scope of this invention.

In a yet still further embodiment, the invention, includes a dental instrument having a voice alert system in any of the above embodiments coupled to an electrical control device. The electrical control device may include a microprocessor and a switch such as an electromechanical switch or a solid state switch. In various embodiments, the electrical control device is adapted to both alert the dental professional of the end of the procedure, and to also turn off the light output, when the predetermined time period has expired. This may further improve the efficiency and accuracy of a dental procedure and free the dental professional to take care of other matters within earshot of the voice alert system rather than having to hover around the patient or be close at hand to turn off the lamp. In one aspect, the alert system may be equipped with a patient to dentist and/or dental practitioner call device.

While preferred embodiments of the invention have been described and illustrated above, it should be understood that these are exemplary of the invention and are not to be considered as limiting. Accordingly, the invention is not to be considered as limited by the foregoing description, but is only limited by the scope of the claims appended hereto.

The invention claimed is:

1. A single-patient light guide comprising:
   a tube having a substantially ellipsoidal cross-section, said tube having a first open end for coupling to a light system;
   a second end with an inter-engaging formation;
      said inter-engaging formation removably coupled to a lip retracting device;
      said lip for retracting device retracts at least a portion of a patient's mouth; and
   a memory circuit in communication with a control system on said light system disposed on the tube for storing a record of a duration of use of the light guide; and
   said control system prevents activation of said light system when said duration of use exceeds a usage limit,
   wherein said ellipsoidal tube has a hollow interior for light from the light system to pass through without being optically affected.

2. The single-patient light guide of claim 1 wherein said memory circuit interfaces with a control disposed externally of the light guide for indicating how long the light guide has been in use.

3. The single-patient light guide of claim 1 further comprising an elastic member mounted to said second end wherein said elastic member forms a cushion between the light guide and the lip retracting device.

4. The light guide of claim 3 wherein the elastic member is made of a material selected from a group consisting of an elastomer, a foam, a biodegradable material and combinations thereof.

5. The light guide of claim 1 wherein said light system comprises at least one heat sink comprising a phase change material.

6. The light guide of claim 1 wherein said light guide comprises a transparent or translucent wall.

7. The light guide of claim 1 wherein the light guide is comprised of a polymer material having a spectral absorption characteristic that passes visible light while absorbing UV light.

8. The light guide of claim 1 wherein the light guide is comprised of a material that reflects at least one range of wavelengths of light.

9. The light guide of claim 1 wherein said tube further comprises at least one air vent.

10. The light guide of claim 1 wherein said memory circuit communicates with said control system through an electromechanical contact or a magnetic contact with the light system.

11. A single-patient light guide comprising:
   a tube having a substantially ellipsoidal cross-section, said tube having a hollow interior;
   a first open end for coupling to a light system;
   a second open end comprising an inter-engaging formation;
   said inter-engaging formation removably coupled to a lip retracting device for retracting at least a portion of a patient's mouth; and a recording device in communication with a control system on said light system coupled to the tube for storing a record of a duration of use signal of the light guide; and said control system prevents activation of said light system if duration of use exceeds a usage limit, wherein the hollow ellipsoidal tube of the light guide allows light from the light system to pass through without being optically affected.

12. The single-patient light guide of claim 11 where said recording device comprises a memory integrated circuit.

13. The single-patient light guide of claim 12 wherein said memory integrated circuit is a write once read many times memory device.

14. The light guide of claim 12 wherein said memory circuit interfaces with a control disposed externally of the light guide for indicating how long the light guide has been in use.

15. The light guide of claim 11 wherein said recording device comprises an electrical contact adapted for mating with an element in the light system to form an electro-mechanical connection.

16. The light guide of claim 11 wherein said recording device communicates with said control system through an electromechanical contact, or a magnetic contact with the light system.

17. The light guide of claim 1 wherein said recording device communicates with said control system through infrared radiation, through wireless radio signals, through light from the visible portion of the electromagnetic spectrum, or through acoustic transmission.

18. The single-patient light guide of claim 11 further comprising an elastic member mounted to said second end wherein said elastic member forms a cushion between the light guide and the lip retracting device.

19. The light guide of claim 11 wherein said light system comprises at least one heat sink comprising a phase change material.

20. A single-patient light guide comprising: a substantially hollow tube having a substantially ellipsoidal cross-section; said substantially hollow tube comprises an opening at each end, and at least one inter-engaging formation at each end; said at least one inter-engaging formation removably coupled to a light system and the other is removably coupled to a lip retracting device; and a memory circuit in communication with a control system on said light system and disposed on the underside of the tube for storing a record of a duration of use of said light guide; and said control system prevents activation of the light system if said duration of use exceeds a usage limit; wherein said light guide allows light from said light system to pass through without being optically affected.

21. The light guide of claim 20 wherein said at least one inter-engaging formation is adapted to inter-engage with at least one corresponding formation in the light system.

22. The light guide of claim 20 wherein said at least one inter-engaging formation is adapted to inter-engage with at least one corresponding formation in a reference device.

23. The light guide of claim 11 wherein said reference device comprises a lip retracting device.

24. The light guide of claim 20 wherein said memory integrated circuit comprises a write once read many times memory device.

25. The light guide of claim 20 wherein said memory circuit interfaces with a control disposed externally of the light guide for indicating how long the light guide has been in use.

26. The light guide of claim 20 wherein said memory circuit communicates with said control system through an electromechanical contact, or a magnetic contact with the light system.

27. The light guide of claim 20 wherein said light system comprises at least one heat sink comprising a phase change material.

* * * * *